United States Patent [19]

Uhlmann et al.

[11] Patent Number: 5,646,261
[45] Date of Patent: Jul. 8, 1997

[54] 3'-DERIVATIZED OLIGONUCLEOTIDE ANALOGS WITH NON-NUCLEOTIDIC GROUPINGS, THEIR PREPARATION AND USE

[75] Inventors: Eugen Uhlmann, Glashütten; Anuschirwan Peyman, Kelkheim, both of Germany; Gerard O'Malley, Newtown, Pa.; Matthias Helsberg, Kelkheim; Irvin Winkler, Liederbach, both of Germany

[73] Assignee: Hoechst Aktiengesellschaft, Frankfurt am Main, Germany

[21] Appl. No.: 5,283

[22] Filed: Jan. 19, 1993

[30] Foreign Application Priority Data

Jan. 22, 1992 [DE] Germany .................. 42 01 663.0

[51] Int. Cl.$^6$ ........................................ C07H 21/04
[52] U.S. Cl. ................................ 536/24.3; 536/24.5
[58] Field of Search ........................ 536/23.1, 24.1, 536/24.3, 24.5, 25.6

[56] References Cited

FOREIGN PATENT DOCUMENTS

| | | |
|---|---|---|
| 0289619 | 11/1988 | European Pat. Off. . |
| 0294196 | 12/1988 | European Pat. Off. . |
| WO84/01778 | 5/1984 | WIPO . |
| WO86/07361 | 12/1986 | WIPO . |
| WO89/12060 | 12/1989 | WIPO . |
| WO91/06556 | 5/1991 | WIPO . |
| 9106626 | 5/1991 | WIPO . |
| WO92/02638 | 2/1992 | WIPO . |
| WO92/06103 | 4/1992 | WIPO . |

OTHER PUBLICATIONS

Froehler et al. (1992) Biochemistry 31: 1603–1609.
Ono et al. (1991) Biochemistry 30: 9914–9921.
Florentiev et al. (1991) Nuc Acid Res Symp. Series No. 24: 167–168.
Jäger et al. (1988) Biochem. 27, 7237–7246.
Verspieren, P., et al., Gene, "An acridine–linked oligodeoxynucleotide targeted to the common 5' end of trypanosome mRNAs kills cultured parasites," 61, pp. 307–315, (1987).
Dolinnaya, N.G., et al., Nucleic Acids Research, "Site–directed modification of DNA duplexes by chemical ligation," 16(9): pp. 3721–3738, (1988).
Seliger, H., Nucleosides & Nucleotides, "Oligonucleotide Analogues with Terminal 3'–3'–and 5'–5'–internucleotidic linkages as antisense inhibitors of viral gene expression," 10(1–3), 469–477 (1991).
Koga, Masakazu, et al., The Journal of Organic Chemistry "Alternating α, β–oligothymidylates with alternating (3'–3')–and (5'–5')–internucleotidic phosphodiester linkages as models for antisense oligodeoxyribonucleotides," 56(12): 3757–3759, (1991).
Shaw, et al., Nucleic Acids Research, "Deoxyoligunucleotides stable to exonuclease degradation in serum," 19(4): 747–750, (1991).
Goodchild, John, Bioconjugate Chemistry, "Conjugates of oligonucleotides and modified oligonucleotides: a review of their synthesis and properties," 1(3): 165–186, (1990).
Uhlmann, E., et al., Chemical Reviews, "Antisense oligonucleotides: a new therapeutic principle," 90(4): 543–584, (1990).
Thuong, N.T., et al., Bulletin de la Societe Chimique de France, "Nouvelle methods de preparation d'esters phosphoriques, renfermant un groupe β–mercaptoethyle, utilisables en synthese nucleotidique," 1–2, pp. II–51–II–56 (1981).

*Primary Examiner*—David Guzo
*Attorney, Agent, or Firm*—Finnegan, Henderson, Farabow, Garrett & Dunner, L.L.P.

[57] ABSTRACT

The present invention relates to novel oligonucleotide analogs with valuable physical, biological and pharmacological properties, and a process for their preparation.

9 Claims, No Drawings

3'-DERIVATIZED OLIGONUCLEOTIDE ANALOGS WITH NON-NUCLEOTIDIC GROUPINGS, THEIR PREPARATION AND USE

DESCRIPTION

The present invention relates to novel oligonucleotide analogs with useful physical, biological and pharmacological properties and a process for their preparation. Their application relates to their use as inhibitors of gene expression (antisense oligonucleotides, ribozymes, sense oligonucleotides and triplex-forming oligonucleotides), as probes for detecting nucleic acids and as aids in molecular biology. Oligonucleotides are being used to an increasing extent as inhibitors of gene expression (G. Zon, Pharmaceutical Research 5, 539 (1988); J. S. Cohen, Topics in Molecular and Structural Biology 12 (1989) Macmillan Press; C. Helene and J. J. Toulme, Biochimica et Biophysica Acta 1049, 99 (1990); E. Uhlmann and A. Peyman, Chemical Reviews 90, 543 (1990)). Antisense oligonucleotides are nucleic acid fragments whose base sequence is complementary to an mRNA which is to be inhibited. These target mRNAs can be of cellular, viral or other pathogenic origin. Suitable cellular target sequences are, for example, those of receptors, enzymes, immunomodulators, ion channels or oncogenies. The inhibition of viral replication using antisense oligonucleotides has been described, for example, for RSV (Rous sarcoma virus), HSV-1 and -2 (herpes simplex virus type I and II), HIV (human immunodeficiency virus) and influenza viruses. In this context oligonucleotides are employed which are complementary to the viral nucleic acid. By contrast, the sequences of sense oligonucleotides are designed in such a way that these oligonucleotides bind ("capture") nucleic acid-binding proteins or nucleic acid-processing enzymes, for example, and thereby inhibit their biological activity (Helene, 1990). Viral targets which can be mentioned here as examples are reverse transcriptase, DNA polymerase and transactivator proteins. Triplex-forming oligonucleotides generally have DNA as their target, and after binding to this DNA form a triple helical structure. While generally the processing splicing etc.) of mRNA and its translation into protein are inhibited using antisense oligonucleotides, triplex-forming oligonucleotides inhibit the transcription or replication of DNA (Helene et al., 1990, Uhlmann and Peyman, 1990). However, it is also possible to bind single-stranded nucleic acids in a first hybridization with an antisense oligonucleotide, with the formation of a double strand which then forms a triplex structure with a triplex-forming oligonucleotide in a second hybridization. In this case the antisense and triplex binding regions can be contained either in two separate oligonucleotides or in one oligonucleotide. The so-called ribozymes, which destroy the target RNA as a result of their ribonuclease activity (J. J. Rossi and N. Sarver, TIBTECH 8, 179 (1990)), represent a further application of synthetic oligonucleotides. Suitably labeled nucleic acid fragments are employed in DNA diagnostic investigation as so-called DNA probes for specific hybridization to a nucleic acid which is to be detected. Here, the specific formation of the new double strand is followed using labeling which preferably is not radioactive. In this way, genetic and malignant diseases, and diseases caused by viruses or other pathogens, can be detected.

In their naturally occurring form, oligonucleotides are little, or not at all, suited for the majority of the said applications. They have to be chemically modified so that they are suitable for the specific requirements. In order that oligonucleotides can be employed in biological systems, for example for inhibition of viral replication, they must fulfil the following preconditions:

1. They must possess a sufficiently high degree of stability under in vivo conditions, that is in serum as well as intracellularly.

2. They must be able to pass through the cell and nuclear membranes.

3. They must bind to their target nucleic acid in a base-specific manner under physiological conditions in order to exert the inhibitory effect.

These preconditions are not essential for DNA probes; however, these oligonucleotides must be derivatized in a manner which permits detection, for example by fluorescence, chemiluminescence, colorimetry or specific staining, (Beck and Köster, Anal. Chem. 62, 2258 (1990)).

Chemical alteration of the oligonucleotides usually takes place by altering the phosphate backbone, the ribose unit or the nucleotide bases in an appropriate manner (Cohen, 1989; Uhlmann and Peyman, 1990). A further method, which is frequently employed, is the preparation of oligonucleotide 5'-conjugates by reacting the 5'-hydroxyl group with appropriate phosphorylation reagents. Oligonucleotides which are only modified at the 5'-end have the disadvantage that they are degraded in serum. If, on the other hand, all the internucleotide phosphate radicals are altered, the properties of the oligonucleotides are often drastically changed. For example, the solubility of the methylphosphonate oligonucleotides in aqueous medium is diminished, as is their ability to hybridize. Phosphorothioate oligonucleotides have non-specific effects, so that, for example, homooligomers are also active against viruses.

Antisense oligonucleotides generally possess a single polarity, which usually exhibits an antiparallel character during hybridization to RNA (see Table 1; A). In certain cases, for example in oligonucleotides composed of α-nucleoside units, the polarity can also be parallel (Table 1; B). Generally depending on the sequence, triplex-forming oligonucleotides can hybridize to double-stranded nucleic acids in a parallel (Table 1; C) or antiparallel (Table 1; D) orientation relative to the purine-rich nucleic acid strand. For this, the base-pairing motifs T•AT, G•GC, C$^+$•GC, G•TA, C$^{Me}$•GC, A•AT and C$^{Pi}$•GC are mainly used, where C$^+$ is a protonated cytosine residue, C$^{Me}$ is a 5-methylcytosine residue, C$^{Pi}$ is a pseudoisocytosine residue and "•" is a Hoogsteen or reverse-Hoogsteen base pairing. However, the use of these Hoogsteen base pairings is restricted to purine-rich regions of the double-stranded nucleic acids.

In order to increase the flexibility of the triplex-forming oligonucleotides with regard to purine-rich target sequences, oligonucleotides with variable polarity were prepared, which oligonucleotides can, because of a (5'5')-strand change (Table 1; E) or a (3'3')-strand change, which changes can optionally alternate (Table 1; F), on each occasion bind purine-rich regions of the opposite strand (Ono et al., Biochemistry (1991) 30, 9914). A strand change while retaining polarity is possible if a (3'5')-spacer is incorporated.

It is additionally possible, using (5'5')-loops (Table 1; G) or (3'5')- or (2'5')-loops, to prepare special antisense oligonucleotides in which one region recognizes a nucleic acid single strand by Watson-Crick base pairing, and a second region recognizes a nucleic acid double strand, arising from Watson-Crick base pairing, by Hoogsteen base pairing. A triplex formation on single-stranded nucleic acids is therefore possible using such antisense/triplex oligonucleotide analogs. In a similar manner, double-stranded sense oligonucleotides, which bind DNA-binding proteins in a sequence-specific manner, can be prepared by way of intramolecular Watson-Crick base pairings (Table 1; I).

Finally, oligonucleotides can be prepared which contain a 5'5'-spacer at the 5'-end (Table 1; K). In these oligonucleotide analogs, both 3'(2')-ends can advantageously contain phosphoryl groups.

TABLE 1

Schematic representation of possible operational principles

| | | |
|---|---|---|
| A | 5'————————3'<br>3'•————5' | antiparallel |
| B | 5'————————3'<br>5'————•3' | parallel |
| C | 5' Pu<br>5'————•3'<br>3'————<br>Py | parallel to the purine-rich strand |
| D | 5' Pu<br>3'•————5'<br>3'————<br>Py | antiparallel to the purine-rich strand |
| E | 5' Pu         Py<br>3'•——5'<br>         5'————•3'<br>3'————————<br>Py         Pu | variable polarity with (5',5')-strand change |
| F | 5' Py        Pu<br>3'•—5'  3'—5'<br>     5'   3'<br>3'———————— | variable polarity with (5'5')- and (3'3')-strand change |
| G |    5'<br>3'•————<br>5'————<br>3'•————<br>    5' | Antisense/triplex oligonucleotide with (5'5')-loop |
| H |    5'<br>3'•————<br>5'————<br>5'————<br>    3' | Antisense/triplex oligonucleotide with (3'5')-loop |
| I |    5'<br>3'•————<br>5'•————<br>    3' | Sense oligonucleotide |
| K | 5'————————<br>3'•—(5'5')—•3' | antisense oligonucleotide with two derivatizable ends |

Those oligonucleotide analogs which have been known hitherto and which obey the operational principles represented in Table 1 C to I generally possess a hydroxyl group at the 3'-end, so that they are degraded in serum, for the most part do not pass easily through membranes, and can only be readily derivatized at the 5'-end.

The object is, therefore, to prepare oligonucleotide analogs with specific hybridization properties toward single-stranded and double-stranded nucleic acids, increased serum stability, good solubility and specific activity.

The invention relates to oligonucleotide analogs of the formula IA and the formula IB

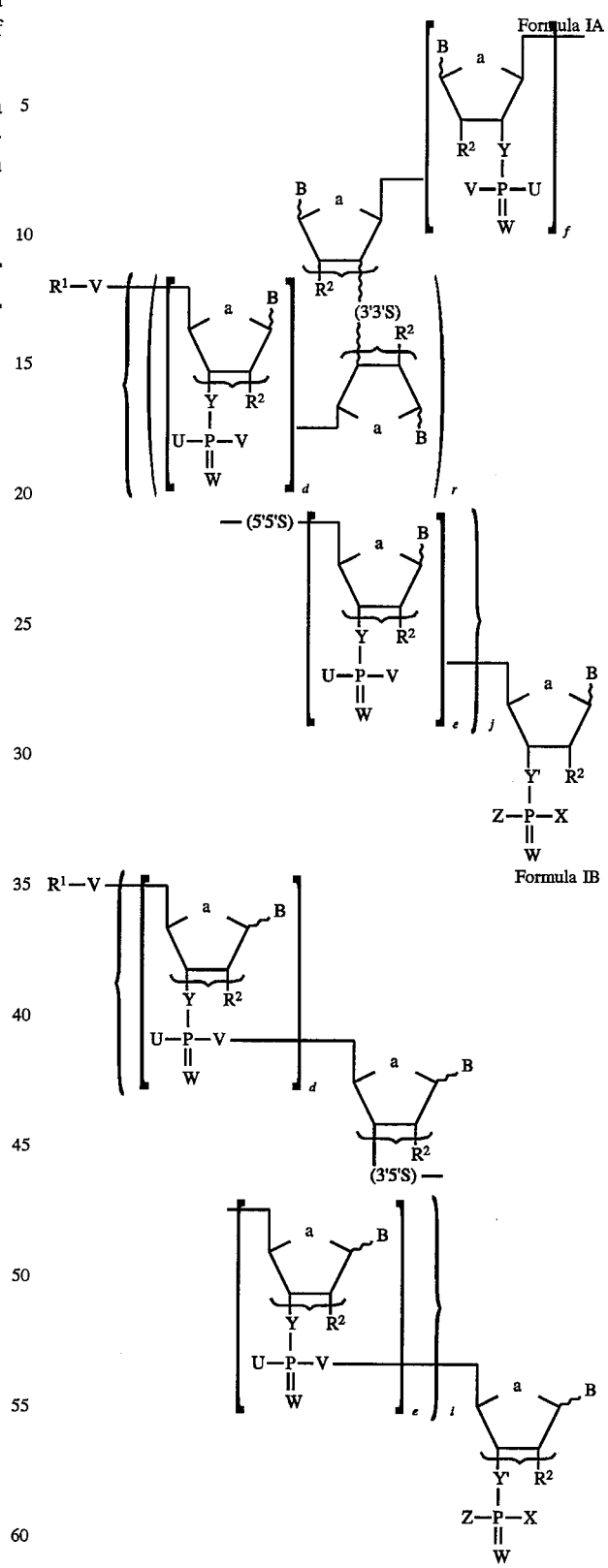

and their physiologically tolerated salts, where $R^1$ is hydrogen, $C_1-C_{18}$-alkyl, preferably $C_1-C_6$-alkyl, $C_2-C_{18}$-alkenyl, $C_2-C_{18}$-alkynyl, $C_2-C_{18}$-alkylcarbonyl, $C_3-C_{18}$-alkenylcarbonyl, $C_3-C_{19}$-alkynylcarbonyl, $C_6-C_{20}$- aryl, $(C_6-C_{14})$-aryl-$(C_1-C_8)$-alkyl, or a radical of the formula II

 (II)

$R^2$ is hydrogen, hydroxyl, $C_1-C_{18}$-alkoxy, halogen, azido or $NH_2$;

B is a conventional base in nucleotide chemistry, for example natural bases such as adenine, cytosine, guanine and thymine or unnatural bases such as purine, 2,6-diaminopurine, 7-deazaadenine, 7-deazaguanine, $N^4N^4$-ethanocytosine, $N^6N^6$-ethano-2,6-diaminopurine, 5-methylcytosine, pseudoisocytosine;

a is oxy or methylene;

d,e,f independently of each other are an integer from 0 to 50, preferably 5 to 15;

i is an integer from 1 to 10, preferably 1 to 3;

r is an integer zero or 1, with the proviso that if r is equal to zero, V is =Y', and if i is greater than 1, r is =1;

W is oxo, selenoxo or thioxo;

V is oxy, thio or imino;

Y is oxy, thio, imino or methylene;

Y' is oxy, thio, imino, $(CH_2)_m$ or $V(CH_2)_m$, where m is an integer from 1 to 18, preferably from 1 to 6;

X is hydroxyl or mercapto;

U is hydroxyl, mercapto, SeH, $C_1-C_{18}$-alkoxy, preferably $C_1-C_6$-alkoxy, $C_1-C_{18}$-alkyl, preferably $C_1-C_6$-alkyl, $C_6-C_{20}$-aryl, $(C_6-C_{14})$-aryl-$(C_1-C_8)$-alkyl, $NHR^3$, $NR^3R^4$ or a radical of the formula $(OCH_2CH_2)_pO(CH_2)_qCH_2R^{11}$, where $R^3$ is $C_1-C_{18}$-alkyl, preferably $C_1-C_8$-alkyl, $C_6-C_{20}$-aryl, $(C_6-C_{14})$-aryl-$(C_1-C_8)$-alkyl, $-(CH_2)_c-[NH(CH_2)_c]_d-NR^{12}R^{12}$, where c is an integer from 2 to 6 and d is an integer from 0 to 6, and each R independently of the other is hydrogen or $C_1-C_6$-alkyl or $C_1-C_{14}$-alkoxy-$C_1-C_6$-alkyl, preferably methoxyethyl;

$R^4$ is $C_1-C_{18}$-alkyl, preferably $C_1-C_8$-alkyl and particularly preferably $C_1-C_4$-alkyl, $C_6-C_{20}$-aryl or $(C_6-C_{10})$-aryl-$(C_1-C_8)$-alkyl, or, in the case of $NR^3R^4$, is, together with $R^3$ and the nitrogen atom carrying them, a 5-6-membered heterocyclic ring, which can additionally contain a further hetero atom selected from the group comprising O, S, N, p is an integer from 1 to 100, preferably 3 to 20 and particularly preferably 3 to 8, q is an integer from 0 to 18, preferably 0 to 15, $R^{11}$ is hydrogen or a functional group such as hydroxyl, amino, $NHR^{13}$, COOH, $CONH_2$, $COOR^{12}$ or halogen, where $R^{12}$ is $C_1-C_4$-alkyl, preferably methyl;

S is a group of the formula III

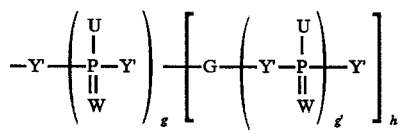 (III)

where g and g' are an integer zero or 1 h is an integer from zero to 10;

G has the meaning $C_1-C_{12}$-alkylene, in particular $C_2-C_4$-alkylene, where alkylene can optionally be substituted by halogen, amino, hydroxyl, $C_1-C_{18}$-alkyl, $C_1-C_{18}$-alkoxy, $C_1-C_{18}$-alkylcarbonyloxy, $C_6-C_{14}$-aryl, $C_6-C_{14}$-aryl-$C_1-C_{18}$-alkyl, or $C_6-C_{14}$-aryl-$C_1-C_8$-alkoxy, $C_6-C_{14}$-aryl-di-$C_1-C_8$-alkylene, $C_6-C_{18}$-arylene, a group of the formula $(CH_2CH_2V)_\alpha CH_2CH_2$ or $(CH_2V)_\alpha CH_2$, where $\alpha$ is an integer from 1 to 11, preferably from 1 to 5, a unit of the formula

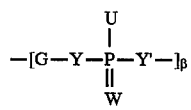

where $\beta$ is an integer from 1 to 6, or a group of the formula

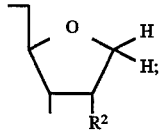

Z=Z' are hydroxyl, mercapto, SeH, $C_1-C_{22}$-alkoxy, preferably $C_6-C_{18}$-alkoxy, $-O-(CH_2)_b-NR^{12}R^{13}$, where b is an integer from 1 to 6, and $R^{13}$ is $C_1-C_6$-alkyl or $R^{12}$ and $R^{13}$ together with the nitrogen atom carrying them form a 3-6-membered ring, $C_1-C_{18}$-alkyl, preferably $C_1-C_8$-alkyl, $C_6-C_{20}$-aryl, $(C_6-C_{14})$-aryl-$(C_1-C_8)$-alkyl, preferably $(C_6-C_{10})$-aryl-$(C_1-C_4)$-alkyl, $(C_6-C_{14})$-aryl-$(C_1-C_8)$-alkoxy, preferably $(C_6-C_{10})$-aryl-$(C_1-C_4)$-alkoxy, where aryl includes heteroaryl, and aryl is optionally substituted by 1, 2 or 3 identical or different radicals selected from the group comprising carboxyl, amino, nitro, $C_1-C_4$-alkylamino, hydroxyl, halogen and cyano, $C_1-C_{18}$-alkylmercapto, $NHR^3$, $NR^3R^4$, a radical of the formula III or a group which favors intracellular uptake or serves as the label for a DNA probe, or, during hybridization of the oligonucleotide analog to the target nucleic acid, attacks the latter with binding, crosslinking or cleavage;

the curved bracket in the 2'- and 3'-position indicates that $R^2$ and the neighboring phosphoryl residue can also be located the opposite way round in the 3'- and 2'-position, where each nucleotide can be present in its D- or L- configuration and the base B can be located in the $\alpha$- or $\beta$-position.

Preferred are oligonucleotide analogs of the formula IA and IB, where the base B is located in the $\beta$-position, the nucleotides are present in the D-configuration, $R^2$ is located in the 2'-position and a is oxy.

Particularly preferred are oligonucleotide analogs of the formula 1A and 1B, where $R^1$ is hydrogen, $C_1-C_6$-alkyl, in particular methyl, or a radical of the formula II;

$R^2$ is hydrogen or hydroxyl, in particular hydrogen;

d, e and f are an integer from 5 to 15;

i is an integer from 1 to 3;

m is an integer from 1 to 6, in particular 1;

U is hydroxyl, mercapto, $C_1-C_6$-alkoxy, $C_1-C_6$-alkyl, $NR^3R^4$ or $NHR^3$, in particular hydroxyl or $C_1-C_6$-alkyl, where $R^3$ is $C_1-C_8$-alkyl, preferably $C_1-C_4$-alkyl, or methoxyethyl, and B, W, V, Y, Y', X and Z have the abovementioned meaning.

Especially preferred are oligonucleotide analogs of the formula IA and IB, where V, Y' and Y have the meaning of oxy. Additionally particularly preferred are oligonucleotide analogs of the formula IA and IB, where V, Y, Y' and W have the meaning of oxy or oxo. Very particularly preferred are oligonucleotide analogs of the formula IA and IB, where V, Y, Y', W and U have the meaning of oxy, oxo or hydroxyl. Furthermore, oligonucleotide analogs of the formula IA and IB are preferred, where $R^1$ is hydrogen. Especially preferred are oligonucleotide analogs of the formula IA and IB, where U, V, W, X, Y' and Y have the meaning of oxy, oxo or hydroxyl and $R^1$ is hydrogen. Very particularly preferred are oligonucleotides of the formula IA, where r is equal to zero, V is the same as Y' and $R^1$ has the meaning of the formula II.

The residues which occur repeatedly, such as $R^2$, B, a, d, e, f, g, g,, h, W, V, Y, Y', U, $R^3$, $R^4$, p, q, G and Z, can, independently of each other, have identical or different meanings, i.e. each V, for example, is, independently of the others, oxy, thio or imino. Halogen is preferably fluorine, chlorine or bromine. Heteroaryl is understood to mean the radical of a monocyclic or bicyclic ($C_3$–$C_9$)-heteroaromatic, which contains one or two N atoms and/or an S or an O atom in the ring system.

Examples of groups which favor intercellular uptake are various lipophilic radicals such as —O—$(CH_2)_x$-$CH_3$, where x is an integer from 6–18, —O—$(CH_2)_n$-CH=CH—$(CH_2)_m$-$CH_3$, where n and m are independently of each other an integer from 6 to 12, —O—$(CH_2CH_2O)_4$-$(CH_2)_9$-$CH_3$, —O—$(CH_2CH_2O)_8$- $(CH_2)_{13}$-$CH_3$ and —O—$(CH_2CH_2O)_7$—$(CH_2)_{15}$-$CH_3$, and also steroid residues, such as cholesteryl, and conjugates which make use of natural carrier systems, such as bile acid, folic acid, 2-(N-alkyl, N-alkoxy)-aminoanthraquinone and conjugates of mannose and peptides of the corresponding receptors, which lead to receptor-mediated endocytosis of the oligonucleotides, such as EGF (epidermal growth factor), bradykinin and PDGF (platelet derived growth factor). Labeling groups are understood to mean fluorescent groups, for example of dansyl (=N-dimethyl-1-amino-naphthyl-5-sulfonyl) derivatives, fluorescein derivatives or coumarin derivatives, or chemiluminescent groups, for example of acridine derivatives, as well as the digoxigenin system, which is detectable by ELISA, the biotin group, which is detectable by the biotin/avidin system, or linker arms with functional groups which allow a subsequent derivatization with detectable reporter groups, for example an aminoalkyl linker, which is reacted with an acridinium active ester to form the chemiluminescent probe. Typical labeling groups are:

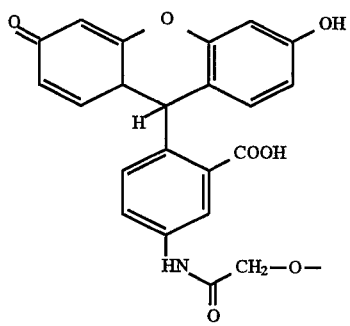

Fluorescein derivative

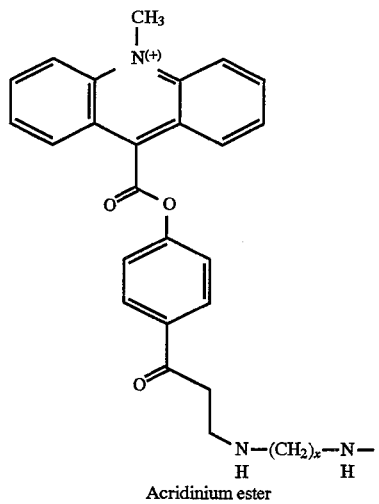

Acridinium ester

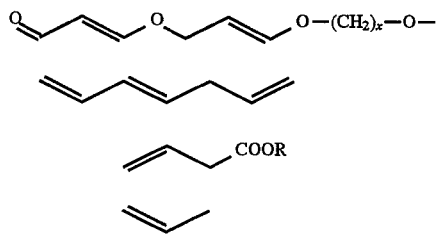

Fluorescein derivative
x = 2–18, preferably 4
R = H or $C_1$–$C_4$-alkyl
( = "fluorescein" for x = 4 and R = $CH_3$)

-continued

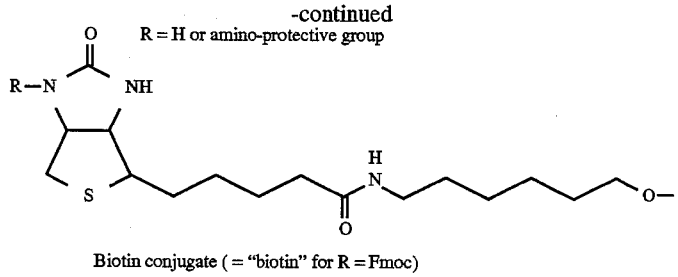

Biotin conjugate ( = "biotin" for R = Fmoc)

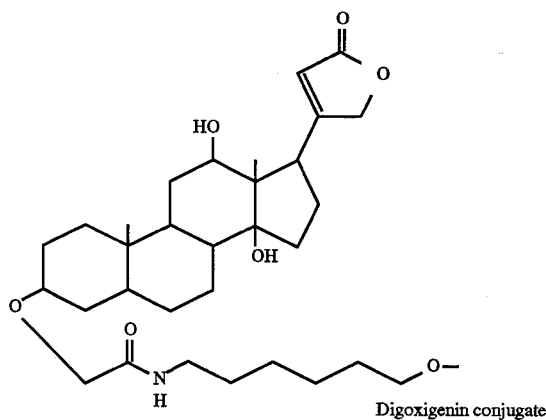

Digoxigenin conjugate

Oligonucleotide analogs which bind to nucleic acids or intercalate and/or cleave or crosslink contain, for example, acridine, psoralen, phenanthridine, naphthoquinone, daunomycin or chloroethylaminoaryl conjugates. Typical intercalating and crosslinking residues are:

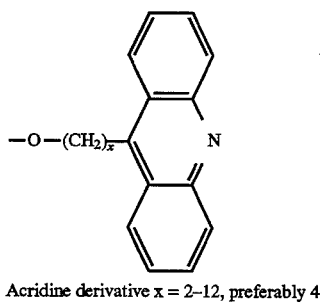

Acridine derivative x = 2–12, preferably 4

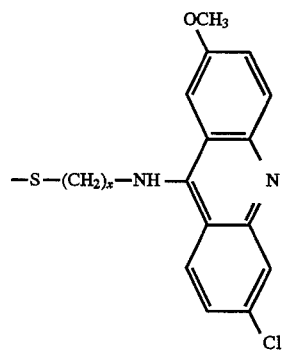

x = 2–12, preferably 4

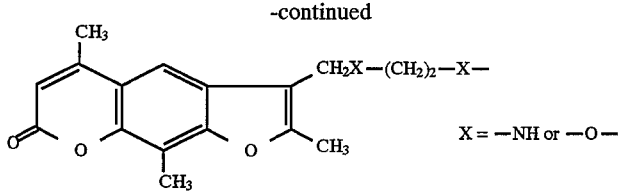
Trimethylpsoralen conjugate ( = "psorolen" for X = 0)
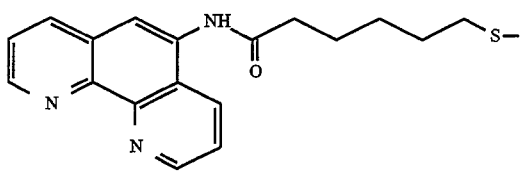
Phenanthroline conjugate
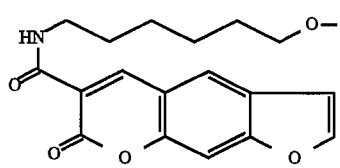
Psoralen conjugate
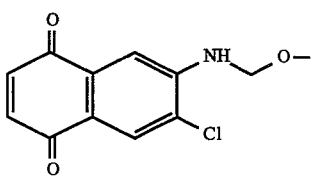
Naphthoquinone conjugate
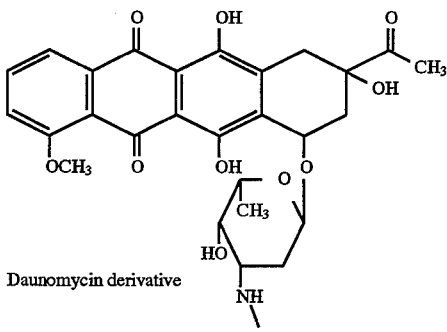
Daunomycin derivative
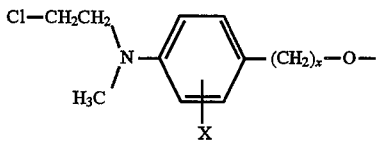
x = 1–18, X = alkyl, halogen, $NO_2$, CN, $-\underset{\underset{O}{\|}}{C}-R$
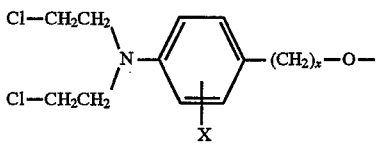
x = 1–18, X = alkyl, halogen, $NO_2$, CN, $-\underset{\underset{O}{\|}}{C}-R-$ The morpholinyl and the imidazolidinyl radicals may be mentioned as examples of $NR^3R^4$ groups in which $R^3$ and $R^4$, together with the nitrogen atom carrying them, form a 5- to 6-membered heterocyclic ring, which additionally contains a further hetero atom.

The invention is not limited to α- and β-D- or L-ribofuranosides, α- and β-D- or L-deoxyribofuranosides and corresponding carbocyclic 5-membered ring analogs, but is also valid for oligonucleotide analogs which are composed of other sugar components, for example ring-expanded and ring-contracted sugars, acyclic sugar derivatives or suitable sugar derivatives of another type. Furthermore, the invention is not limited to the derivatives of the phosphate radical which are cited by way of example in formula IA and IB, but also relates to the known dephospho derivatives.

Oligonucleotide analogs of the formula IA possess one or more 5'5'-spacers (5'5'S) and optionally also one or more 3'3'-spacers (3'3'S) or 2'2'-spacers, which each effect a change in polarity. Oligonucleotide analogs of the formula IB possess a 3'5'-spacer (3'5'S) or (2'5'S), which does not influence polarity, but which, however, permits backfolding of the oligonucleotide analog or a strand change.

Examples of S are propane-1,3-diol phosphates, 2-benzyl- and 2-octadecyl-oxypropane-1,3-diol phosphates, triethylene glycol or hexaethylene glycol phosphates, which can optionally also be repeated. Nucleotide analogs without a heterocyclic base and phenylenedialkylene radicals are further preferred embodiments of S, in particular of (3'3'S). For topological reasons, (5'5'S) is generally longer than (3'3'S). Thus, (5'5'S) possesses at most 20 to 45, preferably 24 to 36, unbranched linkages, while (3'3'S) only has 5 to 15, preferably 6 to 10 unbranched linkages, assuming that a strand change is intended. If, on the other hand, S serves to backfold the oligonucleotide analog, for example to form a triplex on the nucleic acid single strand, lengths of S corresponding to 2 to 8, preferably 4 to 5, nucleotide units are advantageous. By way of example may be mentioned here penta(2-benzyloxy-1,3-propanediol) hexaphosphate and hexa(propane-1,3-diol) pentaphosphate, each of which can effect a (5'5'S) or (3'3'S) linkage.

As for the synthesis of biological oligonucleotides, the preparation of oligonucleotide analogs of the formula IA and IB takes place in solution or preferably in solid phase, optionally with the aid of an automatic synthesis apparatus.

Solid phase synthesis of oligonucleotides with a phosphate or phosphate ester radical at the 3'-end is not possible by the standard phosphoramidite chemistry of Caruthers (M. D. Matteucci and M. H. Caruthers, J. Am. Chem. Soc. 103, 3185 (1981)), since the first nucleotide unit is bound to the solid support via the 3'-hydroxyl group and for this reason oligonucleotides with a 3'-hydroxyl group always result from these syntheses. Various processes based on the solid-phase method have been described, which processes, however, are all laborious and often cannot be used for preparing derivatives such as phosphate esters or alkylphosphonates (R. Eritja et al., Tetrahedron Lett. 32, 1511 (1991); P. Kumar et al., Tetrahedron Lett. 32, 967 (1991); W. T. Markiewicz and T. K. Wyrzykiewicz, Phosphorus, Sulfur and Silicon 51/52, 374 (1990); E. Felder et al., Tetrahedron Lett. 25, 3967 (1984); R. Lohrmann and J. Ruth, DNA 3, 122 (1984)).

The invention relates to a process for preparing oligonucleotide analogs of the formula IA and IB, where a) in the first reaction cycle a nucleotide unit with a 3'(2')-terminal phosphorus(V) grouping and a free 5'-hydroxyl or mercapto group is reacted with a further nucleotide unit within the 3'(2') position a phosphorus(III) or phosphorus(V) grouping or its activated derivative, or with a reagent which permits the introduction of spacer groups, and in the subsequent cycles a nucleotide unit with a 3'(2')- or 5'-terminal phosphorus(III) or phosphorus(V) grouping, or its activated derivative, is reacted with a further nucleotide unit with a 5'- or 3'(2')-terminal free hydroxyl or mercapto group or b) the oligonucleotide analog is constructed with fragments in a similar manner, and protective groups, which have been temporarily introduced in the oligonucleotides obtained according to (a) or (b) in order to protect other functions, are removed and the oligonucleotide analogs of the formula IA and IB thus obtained are, where appropriate, converted into their physiologically tolerated salts.

Employed as starting component for the solid-phase synthesis is a solid support of the formula IV $$D—X'—CH_2CH_2—S(O)_x-CH_2CH_2—A—T \qquad (IV)$$

where

A is a linker arm, which, for example, is a residue of a dicarboxylic acid, a diol, an alkylamine, a dicarboxylic acid monoalkylamide, an acid amide or a phosphate of the formula

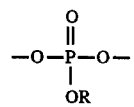

where R is =hydrogen or $C_1$-$C_6$-alkyl which is optionally substituted by —CN, preferably methyl or 2-cyanoethyl, T is a solid support, for example of material such as CPG (controlled pore glass), silica gel or an organic resin such as polystyrene (PS) or a graft copolymer of PS and polyethylene glycol (POE), which is modified in the side chain by functional groups such as hydroxyl, amino, halogen or COOH, D is a protective group which can be removed without cleaving the linker arm A and the X'—$CH_2CH_2$—S(O)$_x$-$CH_2CH_2$— radical (see Bioorg. Chem. 14 (1986) 274–325), such as 4-methoxytetrahydropyranyl and dimethoxytrityl, preferably dimethoxytrityl, x is an integer zero, 1 or 2 and X' is oxy or thio.

The linker arm A, which connects the solid support T to the sulfur-containing radical by a chemical bond (amide, ester inter alia) (Damka et al., Nucleic Acids Res. 18, 3813 (1990)), is preferably a succinic acid residue (O—C(O)—$CH_2CH_2$—C(O)—), an oxalic acid residue (O—C(O)—C(O)—), an alkylamine, preferably LCAA (long chain alkylamine), or polyethylene glycol. A succinic acid residue is particularly preferred. In particular cases, for example in combination with substituents which do not withstand lengthy treatment with ammonia, more labile linkers such as the oxalyl linker are advantageous. The preparation of solid supports of the formulae IV a–c is described in Example 1.

| Support | D | X' | x | A—T |
|---|---|---|---|---|
| IVa | DMTr | O | 2 |  |

-continued

| Support | D | X' | x | A—T |
|---|---|---|---|---|
| IVb | DMTr | O | 2 | —O—C(=O)—(CH₂)₂—C(=O)—N(H)-TentaGel |
| IVc | DMTr | O | 0 | —O—P(=O)(OCH₂—CH₂—CN)—O-TentaGel |

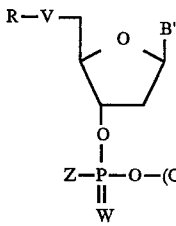

The solid-phase synthesis can take place according to the phosphate triester method, the H-phosphonate method or the phosphoramidite method, preferably according to the phosphoramidite method (E. Sonveaux, Bioorg. Chem. 14, 274 (1986)). The protective group D is always first of all removed from the support of the formula IV by an acid, for example trichloroacetic acid in methylene chloride. In the case of the phosphoramidite method, the support of the formula IV' thus obtained $$HX'—CH_2—CH_2—S(O)_x-CH_2CH_2—A—T \qquad (IV')$$

where x, X', A and T have the abovementioned meaning, is condensed in the presence of a weak acid such as tetrazole with a nucleoside phosphoramidite of the formula V

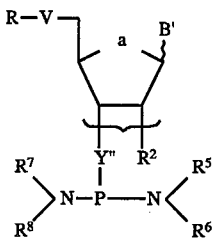

where

B' is B, it being possible for any NH₂ groups present in B to be protected;

R is a protective group which can be removed under mild conditions, such as 4-methoxytetrahydropyranyl or dimethoxytrityl, $R^2$ is hydrogen, alkoxy, halogen or a protected hydroxyl or amino group and $R^5$ and $R^6$ independently of each other are $C_1$–$C_{12}$-alkyl, or both residues together form a 5 to 6-membered ring, Y" is oxy, thio or $(CH_2)_m$, and a, m, V and Z have the abovementioned meaning.

Subsequently, the support thus obtained is oxidized in a manner known per se with iodine water (W=O) or with TETD (tetraethylthiuram disulfide) or elemental sulfur (W=S) or with selenium (W=Se) to form the derivatized support of the formula VII

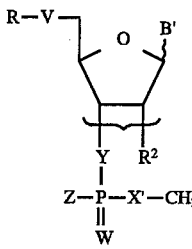

where

R, V, B', $R^2$, Z, X', W, Y", A and T have the abovementioned meaning. Supports of the formula VIIa

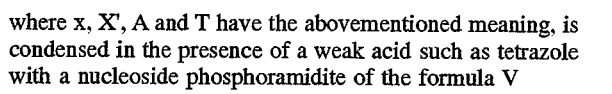

are preferably prepared.

The phosphoramidite of the formula V can be obtained, for example, from the bisamidite of the formula VI

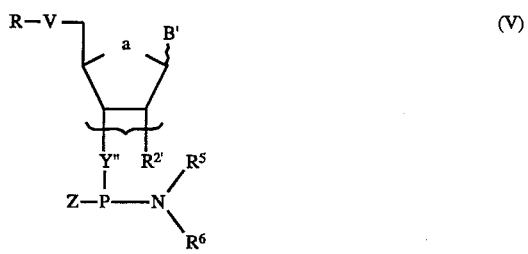

where $R^7$ and $R^8$ are identical to $R^5$ and $R^6$ and a, R, V, B', $R^{2'}$, Y", $R^5$ and $R^6$ have the abovementioned meaning, by reaction with the corresponding alcohol or thioalcohol using tetrazole catalysis (Example 2, Method A), if Z is =alkoxy or alkylmercapto (J. E. Marugg et al., Tetrahedron Lett. 127, 2271 (1986). Preferred bisamidites are those of the formula VIa

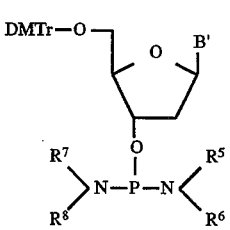

In this way the amidites of the formulae VIII a–m were prepared, for example,

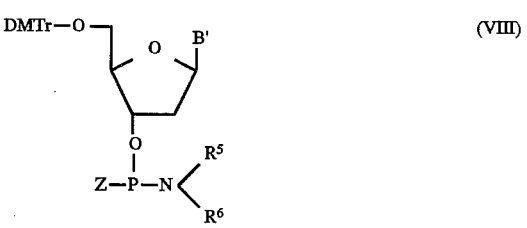

where $R^5$ and $R^6$ have the abovementioned meaning, Z has the meaning of a) $O-CH_2-CH_3$, b) $O\text{-i-}C_3H_7$, c) $O\text{-n-}C_6H_{13}$, d) $O\text{-n-}C_{18}H_{37}$, e) 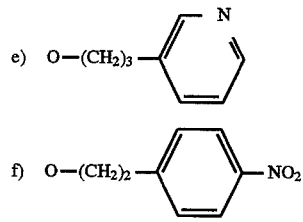

f) 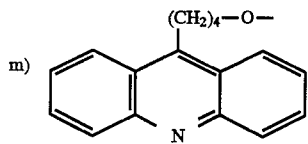

g–k) a residue of the formula III, where in the case of g) p=3 and q=0, h) p=4 and q=9, i) p=5 and q=4 and in the case of k) p=8 and q=13, p) CH3 m) 

and B' is $Cyt^{i-Bu}$ in the case of a), c) and d), Thy in the case of b) and p) and $Cyt^{Bz}$ in the case of e)–k) and m).

An alternative method for loading the support is the reaction of the phosphitylation reagent of the formula IX $$Z''-P\begin{array}{c}R^9\\R^{10},\end{array} \quad (IX)$$

where $R^9$ and $R^{10}$ are, independently of each other, Cl, $NR^5R^6$, $NR^7R^8$, Z" or U' and where U' is $C_1$–$C_4$-alkyl or a hydroxyl group present as a protected derivative, $R^5$, $R^6$, $R^7$ and $R^8$ have the abovementioned meaning, Z" is =Z, with the proviso that hydroxyl, mercapto and SeH must be present as protected derivatives, for example as Y'''—G'—X'—DMTr, where DMTr is dimethoxytrityl, X'=Y'''=oxy or thio, and G' is $(CH_2CH_2O)_\alpha CH_2CH_2$ or $CH_2CH(OR')CH_2$ with R'=$C_1$–$C_{18}$-alkyl, $C_6$–$C_{14}$-aryl or $C_6$–$C_{14}$-aryl-$C_1$–$C_8$-alkyl and α=an integer from 1 to 11, or as $O-CH_2CH_2-CN$, $O-CH_3$, $S-CH_2CH_2CN$, $O-CH_2CH_2-S-CH_2CH_2-O-D$ or

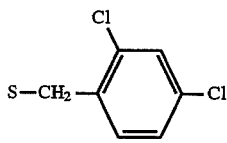

with a nucleoside with a free 3'(2')-group of the formula X

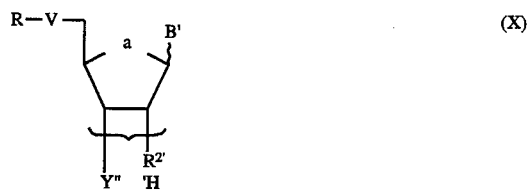

where

V, B', $R^{2'}$ and R have the abovementioned meaning and Y''' is =oxy or thio, and subsequent condensation of the compound thus obtained onto the support of the formula IV' in the presence of a condensing agent, such as tetrasole (for $R^9$, $R^{10}$=$NR^5R^6$ or $NR^7R^8$) or diisopropylamine (for $R^9$, $R^{10}$=Cl). Subsequent oxidation with iodine water or sulfur or selenium then leads to the compound of the formula VIIa. The protective group R can now be removed and the oligonucleotide synthesis continued in a known manner. At the end of the synthesis, the protective groups are removed in a known manner from the support-bound oligonucleotide analog thus obtained, and the oligonucleotide analog of the formula IA or IB according to the invention is then cleaved off the support.

If the synthesis was concluded in the last cycle with a unit of the formula V, an oligonucleotide analog of the formula IA or IB ($R^1$=H) is obtained with a 5'-hydroxyl group and a phosphorus-containing conjugation at the 3'(2')-end. If, on the other hand, a phosphorylating reagent, for example of the formula IX, where $R^9$ is =Z", is employed in the last condensation step, an oligonucleotide analog of the formula IA or IB with $R^1$=formula II, which possesses a phosphate-containing substitution at both the 3'(2')- and 5'-ends, then results from the synthesis. The preparation of oligonucleotides with a 3'(2')-terminal phosphoramidate group is, for example, possible by reaction of the support of the formula IV' with the monomeric methoxyphosphoramidite of the formula V (Z=O—$CH_3$) in the presence of tetrazole, if the oxidation is carried out, as described in Jäger et al. (Biochemistry 27, 7237 (1988), with iodine/$H_2NR^3$ or $HNR^3R^4$, where $R^3$ and $R^4$ have the abovementioned meaning.

In certain cases (Z=$NHR^3$, $NR^3R^4$, O, S or Se) the introduction of the group Z can also take place by the H-phosphonate method, in which the H-phosphonate diester of the formula VII'

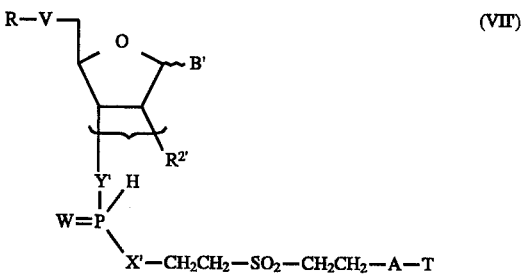

initially formed by reacting a nucleoside phosphonate of the formula XI

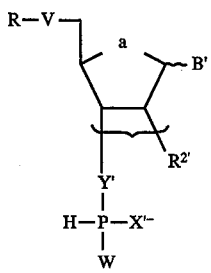
(XI)

where R, V, a, B', Y', X' and W have the abovementioned meaning, with a support of the formula IV', is subjected to an oxidative phosphoramidation (B. Froehler, Tetrahedron Lett. 27, 5575 (1986)). In this way an oglionucleotide with a 3'-terminal cholesteryl group can be prepared, for example, with a cholesteryloxycarbonyl-aminoalkylamine in the presence of carbon tetrachloride.

The preparation of oligonucleotide analogs of the formulae IA and IB is also possible using the triester method, where the group HX' of the support of the formula IV' is reacted with a protected phosphate diester of the formula XII

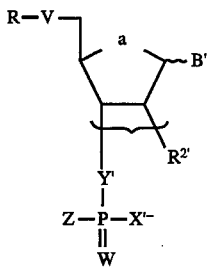
(XII)

where R, V, a, B', $R^{2'}$, Y', Z, W, X' and the curved bracket have the abovementioned meaning, in the presence of a condensing agent, such as an arylsulfonyl chloride and a nucleophilic catalyst such as tetrazole. One possibility for inverting the polarity of an oligonucleotide chain growing in the 3'5'(2'5') direction is by reacting the free 5'-hydroxyl or 5'-thiol group of the growing chain with a unit of the formula XIII, for example with a 3'-O-DMTr-nucleoside 5'-phosphoramidite of the formula XIIIa,

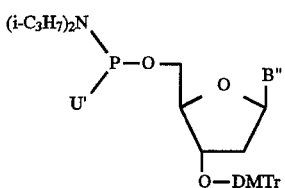

(XIIIa): U'=OCH$_2$CH$_2$CN, B"=B'(XIIIb): U'=CH$_3$, B=H

If oxidation is subsequently carried out with iodine water or sulfur, (5'5'S) then has the meaning of a phosphate (PO$_4^-$) or of a phosphorothioate (PO$_3$S$^-$) radical, respectively. After removing the protective group at the 3'(2')-end, the oligonucleotide chain can, if required, be extended in the 5'3'-direction by successive coupling with units of the formula XIII

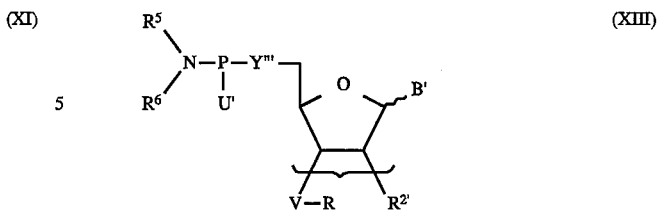
(XIII)

where

U' has the meaning of U, with the proviso that U' is not NHR$^3$ or NR3R$^4$ and hydroxyl, mercapto and SeH are present as protected derivatives (for examples of such derivatives, see Z"), and R$^5$, R$^6$, Y''', V, R, a, R$^{2'}$ and B' have the abovementioned meaning. The synthesis of the units XIII takes place, for example, as described in Seliger et al. (Nucleosides, Nucleotides 10 (1991), 469). If no further inversion takes place, an oligonucleotide analog of the formula IA where r is zero is obtained.

To prepare oligonucleotide analogs of the formula IB, whose polarity is unchanged but whose (3'5'S) nevertheless facilitates backfolding of the chain, the synthesis of the oligonucleotide chain is extended at the the required place using a unit of the formula XIV, which, due to its bifunctionality, can also be multiply condensed.

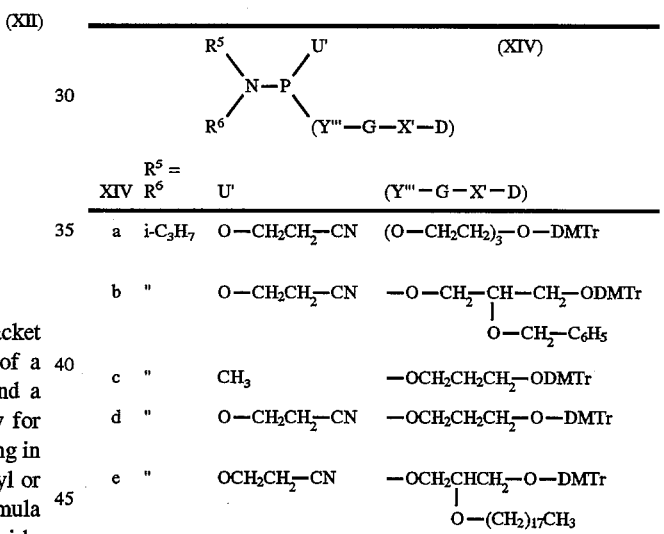

| XIV | $R^5 = R^6$ | U' | (Y'''—G—X'—D) |
|---|---|---|---|
| a | i-C$_3$H$_7$ | O—CH$_2$CH$_2$—CN | (O—CH$_2$CH$_2$)$_3$—O—DMTr |
| b | " | O—CH$_2$CH$_2$—CN | —O—CH$_2$—CH—CH$_2$—ODMTr<br>               \|<br>               O—CH$_2$—C$_6$H$_5$ |
| c | " | CH$_3$ | —OCH$_2$CH$_2$CH$_2$—ODMTr |
| d | " | O—CH$_2$CH$_2$—CN | —OCH$_2$CH$_2$CH$_2$—O—DMTr |
| e | " | OCH$_2$CH$_2$—CN | —OCH$_2$CHCH$_2$—O—DMTr<br>             \|<br>             O—(CH$_2$)$_{17}$CH$_3$ |

For example, a (3'5'S)-loop can be introduced by repeated, preferably 4- to 5-fold, successive coupling with the unit of the formula XIVb. The synthesis is then continued in the 3'5'-direction as described above.

If a strand change is sought in association with hybridization of the oligonucleotide analog to double-stranded nucleic acids, preferably DNA, the 5'5'-spacer must then be of greater length. For example, a triethylene glycol diphosphate can be incorporated at the desired position onto a chain, which has been assembled in the 3'5'-direction, one or more times, preferably twice, by a twice-repeated coupling with the unit of the formula XIVa. In order to alter the polarity, the synthesis is subsequently continued in the 5'3'-direction using nucleotide units of the formula XIII. If a renewed reversal of the polarity is required, a 3'3'-spacer is introduced at the intended position and the synthesis of the chain in the 3'5'-direction is subsequently continued by condensation with nucleoside 3'-phosphoramidites. One example of a 3'3'-spacer is the introduction of a propane-1, 3-diol diphosphate group, which can be introduced by coupling with the unit of the formula XIVd.

If the oligonucleotide synthesis is carried out with the sulfide (x=0) or sulfinyl (x=1) support, these groups are then at the end oxidized to the sulfonyl radical in a manner known per se [Funakoshi et al., Proc. Natl. Acad. Sci. 88 (1991), 6982], in order to ensure ready cleavage with bases, preferably ammonia.

The nature of the amino-protective groups of the bases B' and the constitution of the linker arm A depend, in the individual case, on the nature of the substituent Z, since the latter must be removable without difficulty once synthesis has been completed. For example, in preparing an oligonucleotide 3'-phosphate isopropyl ester (Z=O-i-C—H$_7$), Benzoyl (Bz) protective groups can be used for B=Ade and Cyt and isobutyryl (i-Bu) protective groups for B=Gua. On the other hand, to synthesize an oligonucleotide 3'-methylphosphonate ester (Z=CH$_3$) or ethyl ester (Z=O—C$_2$H$_5$), the more labile phenoxyacetyl (PAC) and isobutyryl protective groups are used for B=Ade and Gua, and for B=Cyt, respectively.

Many conjugates possess additional functional groups, which must be protected in a suitable manner before incorporation into the monomeric units of the formulae V and XIII. For example, the carboxyl group of fluorescein must be protected as an alkyl ester. In psoralen, the amide group can be present as a N-Fmoc (fluorenyl-methoxycarbonyl)-protected compound. Hydroxyl groups can be protected from side reactions by acylation or silylation (t-butyldimethylsilyl). Amino groups can also be present in the trifluoroacetyl-protected form. In exceptional cases, the conjugates may be so unstable that they would be decomposed under the conditions of protective-group removal during the oligonucleotide synthesis. In such cases it is convenient to incorporate only one linker arm with a functional group, for example Z=HN—(CH$_2$)$_x$-NH—Fmoc, where x is an integer from 2–12, preferably 4–6, in the monomer of the formula V. After incor-poration into the oligonucleotide and removal of the protective groups, preferably with ammonia, the free amino group may be coupled to active esters. The baselabile acridinium ester, for example, was prepared in this way.

Characterization of the synthesized oligonucleotide derivatives takes place by electro-spray ionization mass spectrometry (Stults and Masters, Rapid Commun. Mass. Spectr. 5 (1991) 350).

The oligonucleotide analogs of the formula IA and IB according to the invention were tested for their stability in serum and toward known exonucleases.

It was found, surprisingly, that, in comparison with the unmodified oligonucleotides, all oligonucleotide analogs of the formula IA and IB possess markedly increased stability toward the serum nucleases, while their hybridization behavior is only slightly affected.

While unmodified oligonucleotides have a half life of about two hours in fetal calf serum, all oligonucleotide analogs of the formula IA and IB are satisfactorily stable for about 16 hours. In addition, the oligonucleotide analogs of the formula I are stable toward snake venom phosphodiesterase. Unmodified oligonucleotides are degraded exonucleolytically from the 3'-end by snake venom phosphodiesterase and from the 5'-end by spleen phosphodiesterase.

With complementary single-stranded nucleotide sequences, the oligonucleotide analogs of the formula IA and IB form stable, double-stranded hybrids by Watson-Crick base pairing, and stable triplex structures by Watson-Crick and Hoogsteen base pairing, while they form triple helical structures with double-stranded nucleic acids by way of Hoogsteen base pairing, in connection with which the spacers (5'5'S) and (3'3'S) permit a strand change. In this way, the regulation or suppression of biological functions of nucleic acids is possible using the oligonucleotide analogs according to the invention, for example suppression of the expression of cellular genes as well as of oncogenes or of viral genome functions. Oligonucleotide analogs of the formula IA and IB may therefore be employed for the therapy or prophylaxis of viral infections or cancers.

The activity of the oligonucleotides according to the invention was determined on the basis of the inhibition of HSV-1 viral replication.

Sequence I   3'... GCAGGTACAGCCGTTTGTCGA ... 5'RNA-target (SEQ ID NO: 1)
                    ||||||||||||||||||||
             3'     CGTCCATGTCGGCAAACAGCT 3' (SEQ ID NO: 2)
                    ( )
                    (5'5'S)

Sequence II                3' TTGGTGGTGG 5'
                              ||||||||||
             3'... CTCCTGCAAGGAGGACGCCCTTCCG ... 5'-target (SEQ ID NO: 4)
                          ||||||||||||||||||
                          TTCCTCCTGCGGGAAGG (SEQ ID NO: 6)
             (3'5'S)       5'              3'

Sequence III          5'  TTGGTGGTGG 3' (SEQ ID NO: 5)
                          ||||||||||
             3'... CTCCTGCAAGGAGGACGCCCTTCCG ... 5'-target (SEQ ID NO: 6)
                          ||||||||||||||||||
             (5'5'S)      TTCCTCCTGCGGGAAGG (SEQ ID NO: 7)
                          5'              3'

Seqence VI
(AdE1b)      5'    GGGCGGGGCTTAAAGG
                                    (3'5'S)
             3'    CCCGCCCCGAATTTCC           (SEQ ID NO: 8)

-continued

Sequence IV

```
          *3'  5'  3'
           |   A—T
          G • G—C
          G • G—C
          T • A—T
          G • C—G
          T • A—T
          T • A—T
          T • A—T
          G • G—C
          G • T—A
          G • G—C
          G • C—G
          G • C—G
          G • G—C
          T • A—T
          T • A—T
          G • C—G
       5'G • G—C
          C—G • G 5'**
          T—A • T
          T—A • T
          C—G • G
          G—C • G
          C—G • G
          G—C • G
          T—A • T
          T—A • T
          C—G • G
          T—A • T
          C—G • G
          A—T • T
          C—G • G
          T—A   |
          T—A   3'
          T—A
          T—A
           |   |
       *** 3'  5' target

HSV-1 (origin)
*SEQ IDS NO: 9; **SEQ ID NO: 11; ***SEQ ID NO: 10
```

Sequence V

```
         *5'  3' **5'
          |   |   |
          T—A • T
          T—A • T
          C—G • G
          T—A • T
          C—G • G
          A—T • T
          T—A • T
          T—A • T
          C—G • G
          T—A • T
          C—G • G
          T—A • T
          T—A • T
          C—G / ***3'
       3'/ C—G
          T • A—T
          G • G—C
          T • A—T
          T • A—T
          T • A—T
          G • C—G
          G • G—C
        5' C—G • G ****5'
           C—G • G
           T—A • T
           G—C • G
           C—G • G
           C—G • G
           C—G • G
            |   |   |
           3'  5'  3' target
```

APP 770
(Alzheimer)

*SEQ ID NO: 12; SEQ ID NO: 13; *SEQ ID NO: 14;
****SEQ ID NO: 15

In the form of the natural sequence, i.e. without 3'-derivatization and 5'5'-spacer, the selected sequence I is inactive toward HSV-1 in cell culture, since it is subject to rapid degradation in serum. On the other hand, 3'-derivatized oligonucleotide analogs of the formula IA, for example the sequence IA-2 (Example 4b), inhibit HSV-1 replication. The sequence 1 represents only an arbitrary example to illustrate the principle. The sequence 1 is directed against the mRNA of the transactivator protein Vmw65 of MSV-1. The sequences II and III are directed against the splice-acceptor region of the IE4/5 precursor mRNA (IE=immediate early) of HSV-1 and also inhibit HSV-1 replication specifically. An oligonucleotide of the formula IA-4 modified with psoralen at both 3'-ends (Example 4e) of the sequence IV recognizes the origin of replication ($ori_L$) of the genome of HSV-1 and inhibits replication of the latter by triplex formation. The anti-viral activity of the psoralen conjugates may be significantly increased by irradiation with UV light. The HSV-1 genome, with its 160,000 bases, naturally offers innumerable alternative target sequences of diverse efficiency for inhibiting viral replication. By varying the nucleotide sequences, the therapeutic principle may be applied to any other viruses, bacteria or other pathogens. The sole prerequisite for transfer to other pathogens is that the genes which are essential for the life cycle of these pathogens are known. The sequences of these genes are deposited in great variety in the so-called gene databases. This is also the case for oncogenes and other cellular genes whose function is to be suppressed. Examples of other cellular genes are those which encode enzymes, receptors, ion channels, immunomodulators, growth factors and other regulatoryproteins. Sequence V, for example, is directed against the APP770 gene promoter, which is considered responsible for expression of the precursor protein of the plaque-forming amyloid proteins in Alzheimer's disease. As a sense oligonucleotide, sequence VI simulates the SP1 binding region of adenovirus E1b and, as a 3'-modified oligonucleotide analog with a 3'5'-spacer of the formula IB-2, inhibits the transcription of E1b. Examples of oncogenes are abl, neu, myc, myb, ras, fos, mos, erbB, ets, jun, p53, src and rel.

Compared to the oligonucleotide derivatives with a 3'-hydroxyl group, known from the literature, probes for nucleic acids, in particular for DNA, which comprise oligonucleotide analogs of the formula IA and IB on the one hand offer the advantage of increased nuclease stability and on the other permit the acceptance of identical or different marker molecules at both ends of the oligonucleotide. It is of advantage that different marker groupings can be selectively activated within one oligonucleotide (double labeling). The bifunctional derivatization can also be used to introduce a label at the one end and an additional function (for example an affinity label) at the other end. For this purpose, biotin, which recognizes avidin or streptavidin, can, for example, be incorporated at one 3'-end of the oligonucleotide, while an acridinium ester chemiluminescence label can be attached to the other 3'-end via an alkylamino linker.

In addition, the penetration behavior of the oligonucleotide analogs according to the invention is in many cases more favorable than in the case of unmodified oligonucleotides, in particular if lipophilic radicals are introduced. The increased serum stability of the oligonucleotide analogs of the formula IA and IB according to the invention, their improved cell penetration, their improved binding affinity, their ability selectively to destroy target sequences by modification (alkylation, cross-linking), and their improved detectability in DNA diagnostic investigations, are expressed in the form of a higher biological activity as compared with the unmodified oligonucleotides.

The previously mentioned diagnostic, prophylactic and therapeutic applications of the oligonucleotide analogs according to the invention are only a selection of representative examples, and the use of the analogs is therefore not limited to them. In addition, the oligonucleotide analogs according to the invention may, for example, be employed as aids in biotechnology and molecular biology.

The invention relates furthermore to pharmaceutical preparations which contain an effective amount of one or more compounds of the formula IA and/or IB or their physiologically tolerated salts, where appropriate together with physiologically tolerated adjuvants and/or excipients, and/or other known active substances, as well as a process for preparing these preparations, wherein the active substance, together with the excipient and possibly further adjuvants, additives or active substances, is converted into a suitable presentation. Administration preferably takes place intravenously, topically or intranasally.

EXAMPLE 1: Preparation of a Support of the Formula IV a) Preparation of the support of the formula IVa by reacting aminopropyl-CPG with the succinate of bis-hydroxyethyl sulfone dimethoxytrityl ether 4.56 g of the dimethoxytrityl (DMTr) monoether of bis-(2-hydroxyethyl) sulfone (10 mmol) are dried by twice being taken up and concentrated in abs. pyridine, and are dissolved in 25 ml of abs. pyridine, then 1.78 g (14 mmol) of DMAP (dimethylaminopyridine) and 1.4 g of succinic anhydride (14 mmol) are added and this mixture is stirred at room temperature for 3 hours. After the reaction is complete, the mixture is concentrated, the residue is taken up and concentrated three times in toluene to remove the pyridine, and then taken up in 220 ml of methylene chloride. The organic phase is washed with 10% strength citric acid (110 ml) and 3 times with 110 ml of water, dried over sodium sulfate and concentrated. The resulting solid residue is dried in vacuo (5.64 g). 1.67 g (3 mmol) of this succinate are taken up and concentrated twice in abs. pyridine and dissolved in a mixture of 0.65 ml of abs. pyridine and 6 ml of tetrahydrofuran (THF). A solution of 420 mg (3 mmol) of p-nitrophenol and 687 mg of DCC (dicyclohexylcarbodiimide, 3.3 mmol) in 2.1 ml of abs. THF is then added and the mixture is stirred at room temperature for two hours. Once the reaction is complete, the precipitated dicyclohexylurea is removed by centrifugation. The sediment is suspended in 1 ml of abs. ether and centrifuged once again. 1.5 g of the aminopropyl-CPG support from Fluka (500 Å, 100 µmol/g of amino group) are suspended in a mixture of 1.8 ml of abs. DMF and 350 µl of triethylamine, and the combined solutions of the nitrophenyl succinate ester, which have been decanted from the sediment, are added, and the mixture shaken at room temperature for 16 hours. The solid support is separated off and shaken at room temperature for one hour with 3 ml of blocking reagent (acetic anhydride/2,6-lutidine/DMAP; each 0.25 M in THF) to block reactive groups. The derivatized CPG support is then filtered off with suction, washed with methanol, THF, methylene chloride and ether and subsequently dried in vacuo at 40° C. The loading of the support of the formula IVa with dimethoxytrityl-containing component is 38 µmol/g.

b) Preparation of the support of the formula IVb by reacting TentaGel® (®=registered trademark of the Rapp company, Tübingen) with the succinate of the bishydroxy ethyl sulfone dimethoxytrityl ether 100 mg of the amino form of the TentaGel resin, a PS/POE copolymer with 250 µmol/g amino group, are suspended in a mixture of 360 µl of DMF and 70 µl of triethylamine, and 400 µmol of the p-nitrophenyl succinate ester (preparation see Ex. 1a) are added and the mixture is shaken at room temperature for 16 hours. The subsequent workup is as described in Ex. 1a). The loading of the TentaGel resin of the formula IVb with dimethoxytrityl-containing component is 98 µmol/g.

c) Preparation of the support IVc by reacting TentaGel (hydroxy form) with the phosphitylating reagent of the formula IX (Z"—DMTr—O—$CH_2CH_2$—S—$CH_2CH_2$—O—; $R^9$=N(i-$C_3H_7$)$_2$; $R^{10}$=O—$CH_2CH_2CN$).

50 mg of the hydroxy form of the TentaGel resin with 500 µmol/g hydroxyl group are reacted in acetonitrile at 22° C. with 10 equivalents of the phosphitylating reagent of the formula IX (Z"=DMTr—O—$CH_2CH_2$—S—$CH_2CH_2$—O—; $R^9$=N(i-$C_3H_7$)$_2$; $R^{10}$=O—$CH_2CH_2CN$) in the presence of 25 equivalents of tetrazole. After oxidizing with iodine water (1.3 g of iodine in THF/water/pyridine; 70:20:5=v:v:v), working up is carried out as described in Example 1a. The loading of the support of the formula IVc with dimethoxytrityl-containing component is 247 µmol/g.

EXAMPLE 2: Preparation of Protected Nucleoside 3'-phosphoramidites of the Formula VIII a) Preparation of VIIIa (B'=$Cyt^{iBu}$, Z=O—$CH_2CH_3$, $R^5$=$R^6$=i-$C_3H_7$)

2 mmol of the nucleoside 3'-phosphorobisamidite of the formula VI (B'—$Cyt^{iBu}$, $R^5$=$R^6$=$R^7$=$R^8$=i-$C_3H_7$) are taken up and concentrated twice in 20 ml of abs. acetonitrile and then dissolved in 20 ml of abs. acetonitrile. A solution of 2.4 mmol of ethanol and 1.2 mmol of sublimed tetrazole in 5 ml of abs. acetonitrile is then added dropwise over a period of 15 minutes. After stirring has been continued for a further 2.5 hours, the mixture is diluted with 75 ml of methylene chloride, and the organic phase is extracted with 50 ml of 5% strength sodium bicarbonate solution. The aqueous solution is washed twice with 50 ml of methylene chloride, the combined organic phases are dried over sodium sulfate and concentrated in vacuo. The residue is purified by column chromatography on silica gel with methylene chloride/n-heptane/triethylamine (45:45:10;v:v:v). 0.7 g of the required diastereomeric substance is obtained as a compound which is pure by thin-layer chromatography. ($^{31}$P-NMR σ=146.7, 147.5 ppm). Traces of the corresponding bis-ethyl phosphite are isolated as byproduct ($^{31}$P-NMR σ=139.3 ppm).

b) Preparation of VIIIb (B'=Thy, Z=O-i-$C_3H_7$, $R^5$=$R^6$=i-$C_3H_7$)

The preparation takes place byphosphitylation of the 5'-O-dimethoxytritylthymidine of the formula X (B'=Thy (β-position); R=DMTr, V=O, a=O, Y"=O; 2 mmol) with the bisamidite of the formula IX (Z"=O-i-$C_3H_7$, $R^9$=$R^{10}$=N(i-$C_3H_7$)$_2$; 4 mmol) in the presence of tetrazole (0.5 mmol) in 10 ml of abs. methylene chloride. The mixture is worked up as in Example 2a. ($^{31}$P-NMR σ=145.04 ppm, 145.66 ppm).

c) Preparation of VIIIc (B'=$Cyt^{iBu}$, Z=O—n—$C_6H_{13}$, $R^5$=$R^6$=i-$C_3H_7$)

In an analogous manner to Example 2a from the bisamidite of the formula VIa (B'=$Cyt^{iBu}$, $R^5$=$R^6$=$R^7$=$R^8$=i-$C_3H_7$) by reaction with one equivalent of n-hexanol with tetrazole catalysis. ($^{31}$P-NMR 148.1 ppm, 148.5 ppm).

d) Preparation of VIII d (B'=$Cyt^{iBu}$, Z=O—n—$C_{18}H_{37}$, $R^5$=$R^6$=i-$C_3H_7$)

In an analogous manner to Example 2a from the bisamidite of the formula VIa (B'=$Cyt^{iBu}$, $R^5$=$R^6$=$R^7$=$R^8$=i-$C_3H_7$) by reaction with one equivalent of n-octadecanol with tetrazole catalysis. ($^{31}$P-NMR 147.2 ppm, 147.9 ppm).

e) Preparation of VIIIe (B'=$Cyt^{Bz}$, Z=3-pyridylpropan-3-oxy, $R^5$=$R^6$=$R^7$=$R^8$=i-$C_3H_7$)

In an analogous manner to Example 2a from the bisamidite of the formula VIa (B'=$Cyt^{Bz}$, $R^5$=$R^6$=$R^7$=$R^8$=i-$C_3H_7$, $R^{2'}$=H) by reaction with one equivalent of 3-pyridine (propan-3-ol) with tetrazole catalysis. In this case it was possible to separate the two diastereomers by column chromatography. ($^{31}$P-NMR diastereomer 1:147.7 ppm, diastereomer 2:148.2 ppm)

f) Preparation of VIIIf (B'=$Cyt^{Bz}$, Z=p-nitro-phenylethyl-2-oxy, $R^5$=$R^6$=i-$C_3H_7$)

In an analogous manner to Example 2a from the bisamidite of the formula VIa (B'=$Cyt^{Bz}$, $R^5$=$R^6$=$R^7$=$R^8$=i-$C_3H_7$) by reaction with one equivalent of p-nitrophenylethan-2-ol with tetrazole catalysis. ($^{31}$P-NMR 148.1 ppm, 148.6 ppm).

g) Preparation of VIIIg (B'=$Cyt^{Bz}$, Z=—(OCH$_2$CH$_2$)$_3$OCH$_3$, $R^5$=$R^6$=i—$C_3H_7$)

In an analogous manner to Example 2a from the bisamidite of the formula VIa (B'=$Cyt^{Bz}$, $R^5$=$R^6$=$R^7$=$R^8$=i-$C_3H_7$) by reaction with one equivalent of triethylene glycol monomethyl ether with tetrazole catalysis. ($^{31}$P-NMR 148.5 ppm, 148.9 ppm).

h) Preparation of VIIIh (B'=$Cyt^{Bz}$, Z=—(OCH$_2$CH$_2$)$_4$O(CH$_2$)$_9$CH$_3$, $R^5$=$R^6$=i-$C_3H_7$)

In an analogous manner to Example 2a from the bisamidite of the formula VIa (B'=$Cyt^{Bz}$, $R^5$=$R^6$=$R^7$=$R^8$=i-$C_3H_7$) by reaction with one equivalent of tetraethylene glycol monodecyl ether with tetrazole catalysis. ($^{31}$P-NMR 148.4 ppm, 148.8 ppm).

i) Preparation of VIIIi (B'=$Cyt^{Bz}$, Z=—(OCH$_2$CH$_2$)$_5$O(CH$_2$)$_4$CH$_3$, $R^5$=$R^6$=i-$C_3H_7$)

In an analogous manner to Example 2a from the bisamidite of the formula VIa (B'=$Cyt^{Bz}$, $R^5$=$R^6$=$R^7$=$R^8$=i-$C_3H_7$) by reaction with one equivalent of pentaethylene glycol monopentyl ether with tetrazole catalysis. ($^{31}$P-NMR 148.4 ppm, 148.9 ppm).

k) Preparation of VIIIk (B'=$Cyt^{Bz}$, Z=—(OCH$_2$CH$_2$)$_8$O(CH$_2$)$_{13}$CH$_3$, $R^5$=$R^6$=i-$C_3H_7$)

In an analogous manner to Example 2a from the bisamidite of the formula VIa (B'=$Cyt^{Bz}$, $R^5$=$R^6$=$R^7$=$R^8$=i-$C_3H_7$) by reaction with one equivalent of octaethylene glycol monotetradecyl ether with tetrazole catalysis ($^{31}$P-NMR 148.4 ppm, 148.8 ppm).

l) Preparation of VIIIp (B'=Thy, Z=CH$_3$, $R^5$=$R^6$=i-$C_3H_7$)

In an analogous manner to Example 2b from 5'-O-dimethoxytritylthymidine by phosphitylation with the reagent of the formula IX (Z"=CH$_3$, $R^9$=Cl, $R^{10}$=N(i-$C_3H_7$)$_2$, where, instead of tetrazole, catalysis is effected with two equivalents of diisopropylethylamine. ($^{31}$P-NMR 120.6 ppm, 121.0 ppm).

m) Preparation of VIIIm (B'=Cyt$^{Bz}$, Z=acridine-9-(butyl-4-oxy)-, R$^5$=R$^6$=i-C$_3$H$_7$)

In an analogous manner to Example 2a from the bisamidite of the formula VIa (B'=Cyt$^{Bz}$, R$^5$=R$^6$=R$^7$=R$^8$=i-C$_3$H$_7$) by reaction with one equivalent of 9-(4-hydroxybutyl)-acridine with tetrazole catalysis. ($^{31}$P-NMR 146.7 ppm, 147.4 ppm).

EXAMPLE 3: Preparation of the Support-Bound Nucleotide of the Formula VII a) Method A: Preparation of a support of the formula VIIa-1 by coupling the nucleoside 3'-phosphoramidite of the formula VIIIb 7.5 mg of the support from Example 1a, to which is bound 0.2 μmol of the bishydroxyethyl sulfone dimethoxytrityl ether, are treated with 3% strength trichloroacetic acid, thereby removing the DMTr protective group, washed with acetonitrile, and subsequently reacted with 2 μmol of the nucleoside 3'-phosphoramidite of the formula VIIIb (B'=Thy, Z=O-i-C$_3$H$_7$, R$^5$=R$^6$=i-C$_3$H$_7$) in the presence of tetrazole (10 μmol) in acetonitrile. The reaction time is 2.5 minutes. Oxidation with iodine (for W=O; 1.3 g of iodine in THF/water/pyridine; 70:20:5=v:v:v) then takes place.

b) Method B: Preparation of a support of the formula VIIa-2 by reaction via the phosphitylation reagent of the formula IX The phosphitylation reagent of the formula IX (Z"=n-octyl, R$^9$=R$^{10}$=Cl; 1 equivalent) is reacted in the presence of 1.2 equivalents of diisopropylethylamine (DIPEA) in abs. acetonitrile or methylene chloride with a nucleoside of the formula X (1 equivalent of 5'-O-dimethoxytritylthymidine, B'=β-position, Y'''=O) at −78° C. to form the corresponding nucleoside-3'-O-n-octylphosphone monochloride. To remove the protective group D=DMTr, the support of the formula IVa is treated as described in Method A, and then washed with acetonitrile and reacted with an excess of the nucleoside-3'-O-n-octylphosphone monochloride, prepared in situ, in the presence of DIPEA. After oxidation with iodine water, a support-bound nucleotide of the formula VIIa-2 is obtained, which is available for the subsequent oligonucleotide synthesis.

EXAMPLE 4: Preparation of Oligonucleotides of the Formula IA and IB (the monomer is in each case a β-D-deoxyribo-nucleoside)

a) Preparation of an oligonucleotide of the formula IA-1 (R$^1$=R$^2$=H, Z=O-i-C$_3$H$_7$, a=U=V=W=X=Y=Y'=O, B=Thy, e=8, f=r=0, i=1)

T(5'5'p)TpTpTpTpTpTpTpTpTp-(O-i-C$_3$H$_7$) (SEQ ID NO: 16)

0.2 μmol of the support VIIa-1 (B'=Thy, W=O, Z=O-i-C$_3$H$_7$) from Example 3a is treated with the following reagents in turn:

1. abs. acetonitrile
2. 3% trichloroacetic acid in dichloromethane
3. abs. acetonitrile
4. 4 μmol of β-cyanoethyl 5'-O-dimethoxytritylthymidine-3'-phosphite-diisopropylamidite and 25 μmol of tetrazole in 0.15 ml of abs. acetonitrile.
5. Acetonitrile
6. 20% acetic anhydride in THF with 40% lutidine and 10% dimethylaminopyridine
7. Acetonitrile
8. Iodine (1.3 g in THF/water/pyridine; 70:20:5=v:v:v) p The steps 1 to 8, hereinafter termed one reaction cycle, are repeated 7 times to construct the decathymidylate derivative. In the following 9th reaction cycle, the inverse 3'-O—DMTr-nucleoside 5'-phosphoramidite of the formula XIIIa (B'=Thy) is employed for the condensation at step 4 instead of the 5'-O—DMTr-nucleoside 3'-phosphoramidite. After the synthesis has been completed, removal of the dimethoxytrityl group takes place as described in steps 1 to 3. The oligonucleotide is cleaved from the support, and the β-cyanoethyl groups are simultaneously eliminated, by treatment for 1.5 hours with ammonia. Since the oligonucleotide does not contain any amino-protective groups, no further treatment with ammonia is necessary. The resultant crude product of isopropyl decathymidylate 3'-phosphate, which contains a (5'5')-internucleotide bond at the 5'-end, is purified by polyacrylamide gel electrophoresis or HPLC.

b) Preparation of an oligonucleotide of the formula IA-2 (R$^2$=H, Z=O-i-C$_3$H$_7$, a=U=V=W=X=Y=Y'=O; e=19, f=r=0, i=1; R$^1$=formula II, where Z=p-nitrophenylethyl-2-oxy and Z'is =OH)

d(p-Nitrophenylethyl-2-oxy-pC(5'5'p)GpTpCpCpApTpGpTpCpGpGpCpApApApCpApGpCpTp-O-i-C$_3$H$_7$) (SEQ ID NO: 17)

The synthesis takes place in an analogous manner to Example 4a, but with different nucleotide bases in the monomer. In synthesis steps 1 to 8, the monomer is generally employed as β-cyanoethyl 5'-O-dimethoxytrityl-nucleoside-3'-phosphite-dialkylamide, where the amino group of adenine (Ade), cytosine (Cyt) or guanine (Gua) is provided with suitable protective groups. In this example, N$^6$-benzoyl-Ade (Ade$^{Bz}$), N$^4$-benzoyl-Cyt (Cyt$^{Bz}$) amd N$^2$-isobutyryl-Gua (Gua$^{iBu}$) are used. Chain construction takes place as described in Example 4a, starting with the support of the formula VIIa-1 (B'=Thy, W=O, Z=O-i-C$_3$H$_7$), and condensing on the corresponding monomers according to the above sequence. In the 20th reaction cycle, the monomer of the formula XIIIa (B'=Cyt$^{Bz}$) is employed for the condensation. After removing the 3'-O-DMTr group, the free 3'-hydroxyl group is phosphitylated with bis-(p-nitrophenylethyl-2-oxy)-phosphorodiisopropylamide of the formula IX (R$^9$=N(i-C$_3$H$_7$)$_2$, R$^{10}$=Z"=p-nitrophenylethyl-2-oxy) and subsequently oxidized with iodine water. However, to remove the amino-protective groups and one of the two p-nitrophenylethyl groups, an additional treatment with ammonia (50° C. for 16 hours) is carried out.

c) Preparation of an oligonucleotide of the formula IB-1 (R$^1$=R$^2$=H, Z=n—C$_8$H$_{17}$, a=U=V=W=X=Y=Y'=O, i=1, d=9, e=16)

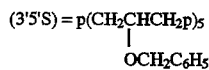

d(GpGpTpGpGpTpGpGpTpT(3'5'S)TpTpCpCpTpCpCpTpGpCpGpGpGpApApGpGp-n—C$_8$H$_{17}$(SEQ ID NO: 18)

Starting with the support of the formula VIIa-2 (B'=Gua$^{PAC}$, W=O, Z=n—C$_8$H$_{17}$), whose preparation takes place in an analogous manner to that described in Example 3b, the chain construction is carried out as in Example 4b. However, the more labile amino-protective groups N$^6$-phenoxyacetyl-Ade (Ade$^{PAC}$), N$^4$-isobutyryl-Cyt (Cyt$^{iBu}$), N$^2$-phenoxyacetyl-Gua (Gua$^{PAC}$), which are easier to cleave at the end of the synthesis, are advantageously used to prepare substitutions (as here for Z=n—C$_8$H$_{17}$) which are base-labile. After the 16th reaction cycle, 5 cycles are carried out with the reagent of the formula XIVb in order to introduce the required (3'5')-spacer. The remaining 10 nucleotide units are then incorporated as described in Example 4a. The cleavage from the support using concentrated ammonia (room temperature for 1.5 hours) is followed by a 6-hour treatment with ethylene-diamine/ethanol/water (5:4:1; v:v:v) to liberate the amino groups of the bases.

d) Preparation of an oligonucleotide of the formula IA-3 ($R^1$=formula II, $R^2$=H, Z=O-i-$C_3H_7$;, a=U=V=W=X=Y=Y'= Z'=O, e=16, f=9, i=1, r=0)

(5'5'S)=p[($CH_2CH_2O$)$_2CH_2CH_2$p]$_2$ d(i-$C_3H_7$-O-pGGTGGTGGTT(5'5'S)TTCCTCCTGCGGGAAGGp-O-i-$C_3H_7$) (SEQ ID NO: 19 and SEQ ID NO: 20, respectively)

The synthesis is carried out initially as described in Example 4b, but starting with the support VIIa-3 (B'=$Gua^{iBu}$, W=O, Z=O-i-$C_3H_7$). After the 16th reaction cycle, two cycles are carried out with the reagent of the formula XIVa in order to introduce the 5'5'-spacer. In the subsequent 10 cycles, the monomeric moieties of the formula XIIIa are employed for the condensation. After removing the 3'-O-DMTr protective group of the last G nucleotide to be added, the free 3'-hydroxyl group is phosphitylated with the cyanoethyloxy-i-propyloxy-phosphoramidite of the formula IX ($R^9$=N(i-$C_3H_7$)$_2$, $R^{10}$=$OCH_2CH_2CN$, Z"=O-i-$C_3H_7$) and subsequently oxidized with iodine water.

e) Preparation of an oligonucleotide of the formula IA-4 ($R^2$=H, Z="psoralen", a=U=V=W=X=Y=Y'=O, e=13, f=15, i=1, r=0; $R^1$=formula II, where Z'=O)
d(3'-"psoralen"-pGpGpTpGpTpTpTpGpGpGpGpGpTpTpGpG(5'5'S)GpTpTpGpGpGpGpT2pTpGpTpGpTpGp-"psoralen") (SEQ ID NO: 21 and SEQ ID NO: 22, respectively)

(5'5'S)=p3'(G)5'-$p_{Me}$-($CH_2$)$_3$-$p_{Me}$-5'(G)3'p

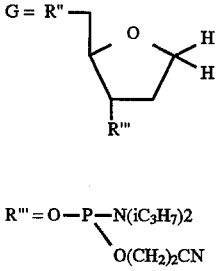

R''' = O—P—N(i$C_3H_7$)2
           \
            O($CH_2$)$_2$CN

The synthesis takes place in an analogous manner to Example 4c, starting with the support of the formula VIIa-4 B'=$Gua^{PAC}$, Z="psoralen", W=0, which was prepared, in an analogous manner to Example 3a, from the monomer of formula VIII (B'=$Gua^{PAK}$, Z="psoralen", $R^5$=$R^6$=i-$C_3H_7$), which was previously obtained, in an analogous manner to Example 2a, from the bisamidite VIa-3 (B'=$Gua^{PAC}$, $R^5$=$R^8$=i-$C_3H_7$) by reaction with "psoralen"-H (U. Pieles and U. Englisch, Nucleic Acids Research (1989) 17, 285). After the 13th reaction cycle, the monomer of the formula XV is used for the coupling in the 14th cycle, as is the monomer of the formula XIVc in the 15th cycle and the monomer of the formula XIIIb in the 16th cycle. In the following 16 cycles the units of the formula XIIIa are once again used for the condensation. After removing the 3'-O-DMTr group, the free 3'-hydroxyl group is phosphitylated with the psoralen phosphoramidite of the formula IX ($R^9$=N(i-$C_3H_7$)$_2$, $R^{10}$=$OCH_2CH_2CN$, Z"="psoralen") and oxidized with iodine water. After removing the protective groups with ammonia, an oligonucleotide of the formula IA-4 is obtained.

f) Preparation of an oligonucleotide of the formula IA-5 ($R^1$=$R^2$=H, Z=—n—$C_8H_{17}$, a=U=V=W=X=Y=Y'=O, d=12, e=f=7, i=r=1)

d(TPTpGpTpGpTpTpTpGpTpGpTpT(3'3'S)TpGpTpTpTpTpGpG(5'5'S)-GpGpTpGpGpGpGpGp-n—$C_8H_{17}$) (SEQ ID NO: 23, SEQ ID NO: 24 and SEQ ID NO: 25, respectively)

(3'3'S)=p($CH_2CH_2CH_2$)p(5'5'S)=as in Example 4e

The preparation takes place in an analogous manner to 4c; however, after the 7th reaction cycle, one cycle is carried out with each of the units of the formulas XV, XIVc and XIIIb in turn in the given sequence in order to introduce (5'5'S). In the following 8 cycles, nucleoside 5'-phosphoramidites of the formula XIIIa are employed. Then, in the next cycle, the incorporation of (3'3'S) takes place with the monomer of the formula XIVd in the coupling step. The remaining 13 cycles take place with the nucleoside 3'-phosphoramidites as in the first 7 cycles. The subsequent procedure is as described in Example 4c.

g) Preparation of an oligonucleotide of the formula IA-6 ($R^1$=formula II, $R^2$=H, Z="fluorescein", a=U=V=W=X=Y=Y'=Z'=O, e=13, f=15, i=1, r=0)

d(3'-"fluorescein"-pGpGpTpGpTpTpTpGpGpGpGpGpTpTpGpG-(5'5'S)GpTpTpGpGpGpGpTpTpGpTpGpTpGp-"fluorescein") (SEQ ID NO: 26 and SEQ ID NO: 27, respectively)

The synthesis takes place in an analogous manner to Example 4e, starting with the support of the formula VIIa-5 (B'=$Gua^{PAC}$, Z="fluorescein", W=O), which, in analogy to Example 3a, was prepared from the monomer of the formula VIII (B'=$Gua^{PAC}$, Z="fluorescein", $R^5$=$R^6$=i-$C_3H_7$), which was previously obtained in an analogous manner to Example 2a from the bisamidite (VIa) (B'=$Gua^{PAC}$, $R^5$=$R^8$=i-$C_3H_7$) by reaction with "fluorescein"-H (Schubert et al., Nucleic Acids Research (1991) 18, 3427). After removing the 3'-O-DMTr group, the free 3'-hydroxyl group is phosphitylated with the fluorescein phosphoramidite of the formula IX ($R^9$=N(i-$C_3H_7$)$_2$, $R^{10}$=$OCH_2CH_2CN$, Z"="fluorescein") and oxidized with iodine water. After removing the protective groups with ammonia, an oligonucleotide of the formula IA-6 is obtained.

h) Preparation of an oligonucleotide of the formula IB-2 ($R^1$=$R^2$=H, Z=O—($CH_2CH_2O$)$_8$($CH_2$)$_3$, a=U=V=W=X=Y=Y'=O, d=e=15, i=1)

(3'5'S)=p($CH_2CH_2CH_2$p)$_4$ d(GpGpGpCpGpGpGpGpCpTpTpApApApGpG(3'5'S)CpCpTpTpTpApApGpCpCpCpCpGpCpCpCp-O—($CH_2CH_2O$)$_8$($CH_2$)$_{13}CH_3$) (SEQ ID NO: 28)

Starting with the support of the formula VIIa-6 (B'=$Cyt^{Bz}$, W=O, Z=—O—($CH_2CH_2O$)$_8$($CH_2$)$_{13}CH_3$), which was prepared using the amidite of the formula VIIIk as described in Example 3a, the oligonucleotide synthesis initially takes place in an analogous manner to Example 4b. After the 15th reaction cycle, 4 cycles are carried out with the unit of the formula XIVd. The remaining 16 nucleo- tides are incorporated as in Example 4b with 5'-O-DMTr-nucleoside 3'-phosphoramidites.

EXAMPLE 5: Testing for Nuclease Stability 10 nmol of the oligonucleotide under investigation are dissolved in 450 µl of 20% strength fetal calf serum in RPMI medium and 50 ml of double-distilled water and incubated at 37° C. 10 μl samples, for gel electrophoresis, and 20 μl samples, for HPLC, are then removed immediately and after 1, 2, 4, 7 and 24 hours and in each case mixed with 5 or 10 μl of formamide, respectively, to stop the reaction, and then heated at 95° C. for 5 minutes. For the gel electrophoresis, the samples are loaded onto a 15% polyacrylamide gel (2% bis), which is then run for about 3,000 volt hours. The bands are visualized by silver staining. For the HPLC analysis, the samples are injected onto a Gen-Pak Fax HPLC column (from Waters/Millipore) and chromatographed at 1 ml/min with 5 to 50% Buffer A in B (Buffer A: 10 mM sodium dihydrogen phosphate, 0.1 M NaCl in acetonitrile/water 1:4 (v:v) pH 6.8; Buffer B: as A, but 1.5 M NaCl).

EXAMPLE 6: Anti-Viral Activity

The anti-viral activity of the compounds according to the invention is examined in in vitro experiments. For this purpose, the compounds according to the invention are added in various dilutions to cell cultures of HeLa and Vero cells in microtiter plates. After 3 h, the cultures are infected with various viruses which are pathogenic for man (e.g.: herpes viruses HSV-1, HSV-2, orthomyxoviruses influenza A2, picornaviruses rhinovirus 2). 48 to 72 h after the infection, therapeutic success is determined on the basis of the cytopathic effect, as measured microscopically, and photometrically following uptake of neutral red (Finter's color test) (Finter, N. B. in "Interferons", N. B. Finter et al., North Holland Publishing Co., Amsterdam, 1966). The minimum concentration at which half the infected cells show no cytopathic effect is considered to be the minimum inhibitory concentration (MIC).

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGCTGTTTGC CGACATGGAC G        21

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..2
        ( D ) OTHER INFORMATION: /note="NN is C(5'5'S)G."

( x i ) SEQUENCE DESCRIPTION: SEQ ID NO:2:

NNTCCATGTC GGCAAACAGC T        21

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 10..11
        ( D ) OTHER INFORMATION: /note="NN is T(3'5'S)T."

( x i ) SEQUENCE DESCRIPTION: SEQ ID NO:3:

GGTGGTGGTN NTCCTCCTGC GGGAAGG　　　　　　　　　　　　　　　　　　　　　　　　27

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCCTTCCCGC AGGAGGAACG TCCTC　　　　　　　　　　　　　　　　　　　　　　　　　　25

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 10
        ( D ) OTHER INFORMATION: /note="The 5'end of SEQ ID
            NO:5 is connected to the 5'end of SEQ ID NO:7
            by a (5'5'S) spacer. N is (5'5'S)T."

( x i ) SEQUENCE DESCRIPTION: SEQ ID NO:5:

NTGGTGGTGG　　　　　　　　　　　　　　　　　　　　　　　　　　　　　　　　　　　　10

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCCTTCCCGC AGGAGGAACG TCCTC　　　　　　　　　　　　　　　　　　　　　　　　　　25

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1
        ( D ) OTHER INFORMATION: /note="The 5'end of SEQ ID
            NO:7 is connected to the 5'end of SEQ ID
            NO:5 by a (5'5'S) spacer. N is (5'5'S)T."

( x i ) SEQUENCE DESCRIPTION: SEQ ID NO:7:

NTCCTCCTGC GGGAAGG　　　　　　　　　　　　　　　　　　　　　　　　　　　　　　17

( 2 ) INFORMATION FOR SEQ ID NO:8:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: misc_feature
      ( B ) LOCATION: 16..17
      ( D ) OTHER INFORMATION: /note="NN is G(3'5'S)C."

( x i ) SEQUENCE DESCRIPTION: SEQ ID NO:8:

GGGCGGGGCT TAAAGNNCTT TAAGCCCCGC CC                32

( 2 ) INFORMATION FOR SEQ ID NO:9:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: misc_feature
      ( B ) LOCATION: 1
      ( D ) OTHER INFORMATION: /note="The 5'end of SEQ ID
         NO:9 is connected to the 5'end of SEQ ID
         NO:11 by a (5'5'S) spacer. N is (5'5'S)G."

( x i ) SEQUENCE DESCRIPTION: SEQ ID NO:9:

NGTTGGGGGT TTGTGG                                  16

( 2 ) INFORMATION FOR SEQ ID NO:10:

( i ) SEQUENCE CHARACTERISTICS:
      ( A ) LENGTH: 35 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:10:

AGGACAAAGT GCGAACGCTT CGCGTTCTCA CTTTT             35

( 2 ) INFORMATION FOR SEQ ID NO:11:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: misc_feature
      ( B ) LOCATION: 1
      ( D ) OTHER INFORMATION: /note="The 5'end of SEQ ID
         NO:11 is connected to the 5'end of SEQ ID
         NO:9 by a (5'5'S) spacer. N is (5'5'S)G."

( x i ) SEQUENCE DESCRIPTION: SEQ ID NO:11:

NTTGGGGTTG TGTG                                    14

( 2 ) INFORMATION FOR SEQ ID NO:12:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:12:

TTCTCATTCT CTTCCAGAAA CGCCTGCCC         29

( 2 ) INFORMATION FOR SEQ ID NO:13:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 13
    ( D ) OTHER INFORMATION: /note="The 3'end of SEQ ID
        NO:13 is connected to the 3'end of SEQ ID
        NO:14 by a (3'3'S) spacer. N is T(3'3'S)."

( x i ) SEQUENCE DESCRIPTION: SEQ ID NO:13:

TTGTGTTTGT GTN         13

( 2 ) INFORMATION FOR SEQ ID NO:14:

( i ) SEQUENCE CHARACTERISTICS:
    ( A ) LENGTH: 7 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1
    ( D ) OTHER INFORMATION: /note="The 5'end of SEQ ID
        NO:14 is connected to the 5'end of SEQ ID
        NO:15 by a (5'5'S) spacer. N is (5'5'S)G."

( i x ) FEATURE:
    ( A ) NAME/KEY: misc_feature
    ( B ) LOCATION: 7
    ( D ) OTHER INFORMATION: /note="The 3'end of SEQ ID
        NO:14 is connected to the 3'end of SEQ ID
        NO:13 by a (3'3'S) spacer. N is T(3'3'S)."

( x i ) SEQUENCE DESCRIPTION: SEQ ID NO:14:

NGTTTGN         7

( 2 ) INFORMATION FOR SEQ ID NO:15:

( i ) SEQUENCE CHARACTERISTICS:
    ( A ) LENGTH: 7 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1
    ( D ) OTHER INFORMATION: /note="The 5'end of SEQ ID
        NO:15 is connected to the 5'end of SEQ ID NO:14 by a (5'5'S) spacer. N is (5'5'S)G."

( x i ) SEQUENCE DESCRIPTION: SEQ ID NO:15:

NGTGGGG         7

( 2 ) INFORMATION FOR SEQ ID NO:16:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..2
    ( D ) OTHER INFORMATION: /note="NN is T(5'5'p)T."

( i x ) FEATURE:
    ( A ) NAME/KEY: misc_feature
    ( B ) LOCATION: 10
    ( D ) OTHER INFORMATION: /note="N is Tp-(O-i-$C_3H_7$)."

( x i ) SEQUENCE DESCRIPTION: SEQ ID NO:16:

NNTTTTTTTN         10

( 2 ) INFORMATION FOR SEQ ID NO:17:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..2
    ( D ) OTHER INFORMATION: /note="NN is
          d(p- Nitrophenylethyl-2-oxy-pC(5'5'p)G."

( i x ) FEATURE:
    ( A ) NAME/KEY: misc_feature
    ( B ) LOCATION: 21
    ( D ) OTHER INFORMATION: /note="N is Tp-O-i-$C_3H_7$."

( x i ) SEQUENCE DESCRIPTION: SEQ ID NO:17:

NNTCCATGTC GGCAAACAGC N         21

( 2 ) INFORMATION FOR SEQ ID NO:18:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 10..11
    ( D ) OTHER INFORMATION: /note="NN is T(3'5'S)Tp."

( i x ) FEATURE:
    ( A ) NAME/KEY: misc_feature
    ( B ) LOCATION: 27
    ( D ) OTHER INFORMATION: /note="N is Gp-n-$C_8H_{17}$."

( x i ) SEQUENCE DESCRIPTION: SEQ ID NO:18:

GGTGGTGGTN NTCCTCCTGC GGGAAGN                                                                            27

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note="The 5'end of SEQ ID
            NO:19 is connected to the 5'end of SEQ ID
            NO:20 by a (5'5'S) spacer. N is T(5'5'S)."

(ix) FEATURE:
        (A) NAME/KEY: misc_feature
        (B) LOCATION: 10
        (D) OTHER INFORMATION: /note="N is i-$C_3H_7$-O-pG."

(xi) SEQUENCE DESCRIPTION: SEQ ID NO:19:

NTGGTGGTGN                                                                                               10

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note="The 5'end of SEQ ID
            NO:20 is connected to the 5'end of SEQ ID
            NO:19 by a (5'5'S) spacer. N is (5'5'S)T."

(ix) FEATURE:
        (A) NAME/KEY: misc_feature
        (B) LOCATION: 17
        (D) OTHER INFORMATION: /note="N is Gp-O-i-C3H7."

(xi) SEQUENCE DESCRIPTION: SEQ ID NO:20:

NTCCTCCTGC GGGAAGN                                                                                       17

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note="The 5'end of SEQ ID
            NO:21 is connected to the 5'end of SEQ ID NO:22
            by a (5'5'S) spacer. N is (5'5'S)G."

(ix) FEATURE:
        (A) NAME/KEY: misc_feature
        (B) LOCATION: 16
        (D) OTHER INFORMATION: /note="N is "psoralen"-pG."

(xi) SEQUENCE DESCRIPTION: SEQ ID NO:21:

NGTTGGGGGT TGTGN                        16

(2) INFORMATION FOR SEQ ID NO:22:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note="The 5'end of SEQ ID NO:
            22 is connected to the 5'end of SEQ ID NO:21
            by a (5'5'S) spacer. N is (5'5'S)G."

(ix) FEATURE:
        (A) NAME/KEY: misc_feature
        (B) LOCATION: 14
        (D) OTHER INFORMATION: /note="N is Gp-"psoralen.""

(xi) SEQUENCE DESCRIPTION: SEQ ID NO:22:

NTTGGGGTTG TGTN                         14

(2) INFORMATION FOR SEQ ID NO:23:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 13
        (D) OTHER INFORMATION: /note="The 3'end of SEQ ID
            NO:23 is connected to the 3'end of SEQ ID
            NO:24 by a (3'3'S) spacer. N is T(3'3'S)."

(xi) SEQUENCE DESCRIPTION: SEQ ID NO:23:

TTGTGTTTGT GTN                          13

(2) INFORMATION FOR SEQ ID NO:24:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note="The 5'end of SEQ ID
            NO:24 is connected to the 5'end of SEQ ID
            NO:25 by a (5'5'S) spacer. N is G(5'5'S)."

(ix) FEATURE:
        (A) NAME/KEY: misc_feature
        (B) LOCATION: 8
        (D) OTHER INFORMATION: /note="The 3'end of SEQ ID
            NO:24 is connected to the 3'end of SEQ ID
            NO:23 by a (3'3'S) spacer. N is (3'3'S)T."

(xi) SEQUENCE DESCRIPTION: SEQ ID NO:24:

NGTTTTGN                                8

( 2 ) INFORMATION FOR SEQ ID NO:25:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1
        ( D ) OTHER INFORMATION: /note="The 5'end of SEQ ID
            NO:25 is connected to the 5'end of SEQ ID
            NO:24 by a (5'5'S) spacer. N is (5'5'S)G."

( i x ) FEATURE:
        ( A ) NAME/KEY: misc_feature
        ( B ) LOCATION: 8
        ( D ) OTHER INFORMATION: /note="N is Gp-n-C8H17."

( x i ) SEQUENCE DESCRIPTION: SEQ ID NO:25:

NGTGGGGN        8

( 2 ) INFORMATION FOR SEQ ID NO:26:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1
        ( D ) OTHER INFORMATION: /note="The 5'end of SEQ ID
            NO:26 is connected to the 5'end of SEQ ID
            NO:27 by a (5'5'S) spacer. N is G(5'5'S)."

( i x ) FEATURE:
        ( A ) NAME/KEY: misc_feature
        ( B ) LOCATION: 16
        ( D ) OTHER INFORMATION: /note="N is "fluoroscein"-pG."

( x i ) SEQUENCE DESCRIPTION: SEQ ID NO:26:

NGTTGGGGGT TTGTGN        1 6

( 2 ) INFORMATION FOR SEQ ID NO:27:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1
        ( D ) OTHER INFORMATION: /note="The 5'end of SEQ ID
            NO:27 is connected to the 5'end of SEQ ID
            NO:26 by a (5'5'S) spacer. N is (5'5'S)G."

( i x ) FEATURE:
        ( A ) NAME/KEY: misc_feature
        ( B ) LOCATION: 14
        ( D ) OTHER INFORMATION: /note="N is Gp-"fluorescein.""

( x i ) SEQUENCE DESCRIPTION: SEQ ID NO:27:

NTTGGGGTTG TGTN                                                       14

( 2 ) INFORMATION FOR SEQ ID NO:28:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: misc_feature
      ( B ) LOCATION: 16..17
      ( D ) OTHER INFORMATION: /note="NN is G(3'5'S)Cp."

( i x ) FEATURE:
      ( A ) NAME/KEY: misc_feature
      ( B ) LOCATION: 32
      ( D ) OTHER INFORMATION: /note="N is
            Cp-O- (CH₂CH₂)₈(CH₂)₁₃CH₃)."

( x i ) SEQUENCE DESCRIPTION: SEQ ID NO:28:

GGGCGGGGCT TAAAGNNCTT TAAGCCCCGC CN                                    32

What is claimed is:

1. An oligonucleotide analog of the formula IA or IB

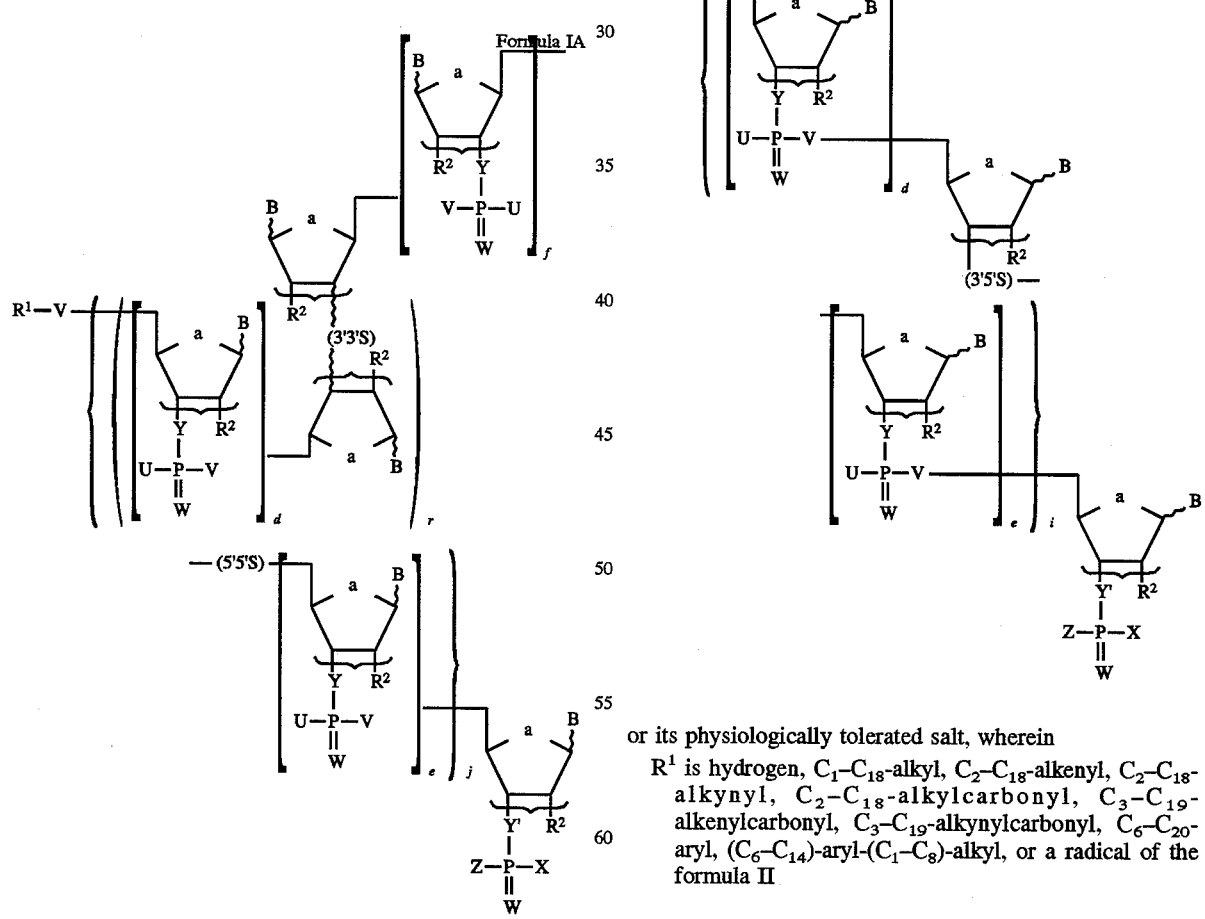

or its physiologically tolerated salt, wherein $R^1$ is hydrogen, $C_1$–$C_{18}$-alkyl, $C_2$–$C_{18}$-alkenyl, $C_2$–$C_{18}$-alkynyl, $C_2$–$C_{18}$-alkylcarbonyl, $C_3$–$C_{19}$-alkenylcarbonyl, $C_3$–$C_{19}$-alkynylcarbonyl, $C_6$–$C_{20}$-aryl, ($C_6$–$C_{14}$)-aryl-($C_1$–$C_8$)-alkyl, or a radical of the formula II $$Z-\underset{\underset{W}{\parallel}}{\overset{|}{P}}-Z'; \qquad (II)$$

$R^2$ is hydrogen, hydroxyl, $C_1$–$C_{18}$-alkoxy, halogen, azido or $NH_2$;

B is a conventional base in nucleotide chemistry;

a is oxy or methylene;

d,e,f independently of each other are an integer from 0 to 50;

i is an integer from 1 to 10;

r is an integer zero or 1, with the proviso that if r is equal to zero, V is =Y', and if i is greater than 1 r is =1;

w is oxo, selenoxo or thioxo;

v as oxy, thio or imino;

Y is oxy, thio, imino or methylene;

Y' as oxy, thio, imino, $(CH_2)_m$ or $V(CH_2)_m$, where m as an integer from 1 to 18;

X is hydroxyl or mercapto;

U is hydroxyl, mercapto SeH, $C_1$–$C_{18}$-alkoxy, $C_1C_{18}$-alkyl, $C_6$–$C_{20}$-aryl, $(C_6$–$C_{14})$-aryl-$(C_1$–$C_8)$-alkyl, $NHR^3$, $NR^3R^4$ or a radical of theformula$(OCH_2CH_2)_pO(CH2)CH_2R_{11}$ where $R^3$ is $C_1$–$C_{18}$-alkyl, $C_6$–$C_{20}$-aryl, $(C_6$–$C_{14})$-aryl-$(C_1$–$C_8)$-alkyl, $-(CH_2)_c$-$[NH(CH_2)_c]_d$-$NR^{12}R^{12}$, where c is an integer from 2 to 6 and d is an integer from 0 to 6, and each $R^{12}$ independently of the other is hydrogen or $C_1$–$C_6$-alkyl or $C_1$–$C_4$-alkoxy-$C_1$–$C_6$-alkyl;

$R^4$ is $C_1$–$C_{18}$-alkyl, $C_6$–$C_{20}$-aryl or $(C_6$–$C_{10})$-aryl-$(C_1$–$C_8)$-alkyl, or, in the case of $NR^3R^4$, is, together with $R^3$ and the nitrogen atom carrying them, a 5-6-membered heterocyclic ring, which can additionally contain a further hetero atom selected from the group consisting of O, S, and N, p is an integer from 1 to 100, q is an integer from 0 to 18, $R^{11}$ is hydrogen or a functional group;

S is a group of the formula III

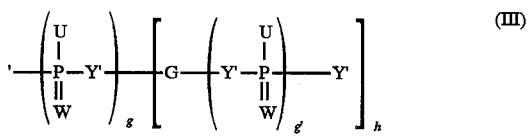

where g and g' are an integer zero or 1 h is an integer from zero to 10;

G is $C_1$–$C_{12}$-alkylene, where one or more positions of alkylene can optionally be substituted by halogen, amino, hydroxyl, $C_1$–$C_{18}$-alkyl, $C_1$–$C_{18}$-alkoxy, $C_1$–$C_{18}$-alkylcarbonyloxy, $C_6$–$C_{14}$-aryl, $C_6$–$C_{14}$-aryl-$C_1$–$C_{18}$-alkyl, or $C_6C_{14}$-aryl-$C_1$–$C_8$-alkoxy, $C_6$–$C_{14}$-aryl-di-$C_1$–$C_8$-alkylene, $C_6$–$C_{18}$-arylene, a group of the formula $(CH_2CH_2V)_\alpha CH_2CH_2$ or $(CH_2V)_{60}CH_2$, where $\alpha$ is an integer from 1 to 11, a unit of the formula

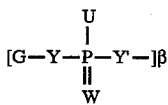

where $\beta$ is an integer from 1 to 6, or a group of the formula

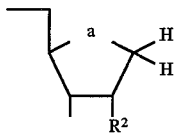

Z=Z' are hydroxyl, mercapto, SeH, $C_1$–$C_{22}$-alkoxy, —O—$(CH_2)_b$-$NR^{12}R^{13}$, where b is an integer from 1 to 6, and $R^{13}$ is $C_1$–$C_6$-alkyl or $R^{12}$ and $R^{13}$ together with the nitrogen atom carrying them form a 3-6-membered ring, $C_1$–$C_{18}$-alkyl, $C_6$–$C_{20}$-aryl, $(C_6$–$C_{14})$-aryl-$(C_1$–$C_8)$-alkyl, $(C_6$–$C_{14})$-aryl-$(C_1$–$C_8)$-alkoxy, where aryl includes heteroaryl, and aryl is optionally substituted by 1, 2 or 3 identical or different radicals selected from the group consisting of carboxyl, amino, nitro, $C_1$–$C_4$-alkylamino, hydroxyl, halogen and cyano, $C_1$–$C_{18}$-alkylmercapto, $NHR^3$, $NR^3R^4$, a radical of the formula III, a group which favors intracellular uptake, a labeling group, a binding group, an intercalating group, a cleavage group, and a crosslinking group;

the curved bracket in the 2'- and 3'-position indicates that $R^2$ and the neighboring phosphoryl residue can also be located the opposite way round in the 3'- and 2'-position, where each nucleotide can be present in its D- or L-configuration and the base B can be located in the $\alpha$ or $\beta$-position, with the proviso that, if Z=hydroxyl, mercapto, methyl, or ethoxy, at least one of the groups X, Y, Y', V, and W is not hydroxyl, oxy, or oxo, or $R^1$ is not hydrogen.

2. The oligonucleotide analog as claimed in claim 1, wherein the base B is located in the $\beta$-position, the nucleotides are present in the D-configuration, $R^2$ is located in the 2'-position and a is oxy.

3. The oligonucleotide analog as claimed in claim 1, wherein $R^1$ is hydrogen, $C_1$–$C_6$-alkyl, or a radical of the formula II;

$R^2$ is hydrogen or hydroxyl;

d, e and f are an integer from 5 to 15;

i is an integer from 1 to 3;

m is an integer from 1 to 6;

U is hydroxyl, mercapto, $C_1$–$C_6$alkoxy, $C_1$–$C_6$-alkyl, $NR^3R^4$ or $NHR^3$, where $R^3$ is $C_1$–$C_8$-alkyl or methoxymethyl.

4. The oligonucleotide analog as claimed in claim 1 wherein $R^1$ is hydrogen, $C_1$–$C_6$-alkyl, or a radical of the formula II

$R^2$ is hydrogen, hydroxyl, or $C_1$–$C_{18}$-alkoxy;

B is a conventional base in nucleotide chemistry;

a is oxy or methylene;

d,e,f independently of each other are an integer from 0 to 19;

i is an integer from 1 to 3;

r is an integer zero or 1, with the proviso that if r is equal to zero, V is =Y', and if i is greater than 1, r is =1;

W is oxo, selenoxo or thioxo;

V is oxy, thio or imino;

Y is oxy, thio, imino or methylene;

Y' is oxy, thio, imino, $(CH_2)_m$ or $V(CH_2)_m$, where m is an integer from 1 to 6;

X is hydroxyl or mercapto;

U is hydroxyl, mercapto, $C_1-C_6$-alkoxy, $C_1-C_6$-alkyl, $NHR^3$, $NR^3R^4$, where $R^3$ is $C_1-C_8$-alkyl or methoxyethyl;

$R^4$ is $C_1-C_8$-alkyl;

S is a group of the formula III

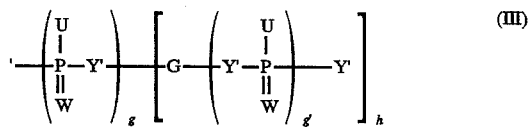
(III)

where g and g' are an integer zero or 1 h is an integer from zero to 10;

G is $C_1-C_{12}$-alkylene, where one or more positions of alkylene can optionally be substituted by halogen, amino, hydroxyl, $C_1-C_{18}$-alkyl, $C_1-C_{18}$-alkoxy, $C_1-C_{18}$-alkylcarbonyloxy, $C_6-C_{14}$-aryl, $C_6-C_{14}$-aryl-$C_1-C_{18}$-alkyl, or $C_6-C_{14}$-aryl-$C_1-C_8$-alkoxy, $C_6-C_{14}$-aryl-di-$C_1-C_8$-alkylene, $C_6-C_{18}$-arylene, a group of the formula $(CH_2CH_2V)_\alpha CH_2CH_2$ or $(CH_2V)_\alpha CH_2$, where $\alpha$ is an integer from 1 to 11, a unit of the formula

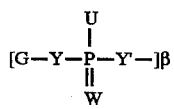

where $\beta$ is an integer from 1 to 6, or a group of the formula

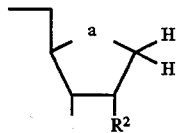

Z=Z' are hydroxyl, mercapto, SeH, $C_3-C_{18}$-alkoxy, $-O-(CH_2)_b-NR^{12}R^{13}$, where b is an integer from 1 to 6, and $R^{13}$ is $C_1-C_6$-alkyl or $R^{12}$ and $R^{13}$ together with the nitrogen atom carrying them form a 3-6-membered ring, $C_1-C_8$-alkyl, $C_6-C_{20}$-aryl, $(C_6-C_{10})$-aryl $(C_1-C_4)$-alkyl, $(C_6-C_{10})$-aryl-$(C_1-C_4)$-alkoxy, where aryl includes heteroaryl, and aryl is optionally substituted by 1, 2 or 3 identical or different radicals selected from the group consisting of carboxyl, amino, nitro, $C_1-C_4$-alkylamino, hydroxyl, halogen and cyano, $C_1-C_{18}$-alkylmercapto, $NHR^3$, $NR^3R^4$, a radical of the formula III, $-O-(CH_2)_x-CH_3$, where x is an integer from 6-18, $-O-(CH_2)_n-CH=CH-(CH_2)_m-CH_3$, where n and m are independently of each other an integer from 6 to 12, $-O-(CH_2CH_2O)_4-(CH_2)_9-CH_3$, $-O-(CH_2CH_2O)_8-(CH_2)_{13}-CH_3$, and $-O-(CH_2CH_2O)_7-(CH_2)_{15}-CH_3$, cholesteryl, bile acid, folic acid, 2-(N-alkyl, N-alkoxy)-aminoanthraquinone, conjugates of mannose, EGF (epidermal growth factor), bradykinin, PDGF (platelet derived growth factor), dansyl (=N-dimethyl-1-amino-naphthyl-5-sulfonyl) derivatives, fluorescein derivatives or coumarin derivatives, acridine derivatives, digoxigenin, biotin, an aminoalkyl linker, which is reacted with an acridinium active ester, acridine derivatives, psoralen derivatives, phenanthridine derivatives, naphthoquinone derivatives, daunomycin derivatives or chloroethylaminoaryl derivatives.

5. The oligonucleotide analog as claimed in claim 1, wherein V, Y and Y' are oxy.

6. The oligonucleotide analog as claimed in claim 1, wherein W is oxo.

7. The oligonucleotide analog as claimed in claim 1, wherein U is hydroxyl.

8. The oligonucleotide analog as claimed in claim 1, wherein $R^2$ is hydrogen.

9. A process for preparing an oligonucleotide analog of the formula IA or IB or salt thereof as claimed in claim 1, wherein a) in the first reaction cycle a nucleotide unit with a 3'(2')-terminal phosphorus(V) grouping and a free 5'-hydroxyl or mercapto group is reacted with a further nucleotide unit with in the 3'(2') position a phosphorus (III) or phosphorus(V) grouping or its activated derivative, or with a reagent which permits the introduction of spacer groups, and in the subsequent cycles a nucleotide unit with a 3'(2')- or 5'-terminal phosphorus(III) or phosphorus(V) grouping, or its activated derivative, is reacted with a further nucleotide unit with a 5'- or 3'(2')-terminal free hydroxyl or mercapto group or b) the oligonucleotide analog is constructed with fragments in a similar manner, and protective groups, which have been temporarily introduced in the oligonucleotides obtained according to (a) or (b) in order to protect other functions, are removed and the oligonucleotide analog of the formula IA and IB thus obtained is, where appropriate, converted into its physiologically tolerated salt.

* * * * *

UNITED STATES PATENT AND TRADEMARK OFFICE
CERTIFICATE OF CORRECTION

PATENT NO. : 5,646,261
DATED : July 8, 1997
INVENTOR(S) : Eugen UHLMANN ET AL.

It is certified that error appears in the above-indentified patent and that said Letters Patent is hereby corrected as shown below:

Claim 1, column 49, line 30, in Formula IA,

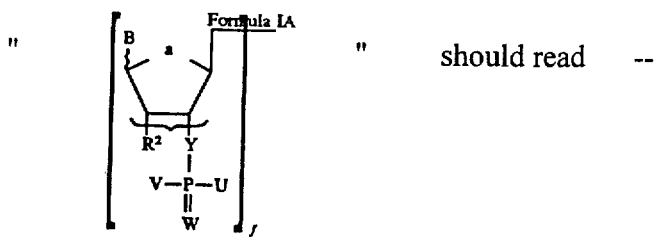

Claim 1, column 49, line 57, in Formula IA, "$;$" should read --$,$--;

Claim 1, column 51, line 24, "theformula($OCH_2CH_2$)$p$ O(CH2)$CH_2R_{11}$" should read --the formula $(OCH_2CH_2)p$ $O(CH_2)qCH_2R_{11}$--.

Claim 1, column 51, line 59, "$(CH_2V)_{60}$ $CH_2$" should read --$(CH_2V)_\alpha CH_2$--.

Claim 3, column 52, line 46, "methoxymethyl" should read --methoxyethyl--.

Claim 4, column 52, line 47, after "claim 1" insert --,--.

UNITED STATES PATENT AND TRADEMARK OFFICE
CERTIFICATE OF CORRECTION

PATENT NO. : 5,646,261
DATED : July 8, 1997
INVENTOR(S) : Eugen UHLMANN ET AL.

It is certified that error appears in the above-identified patent and that said Letters Patent is hereby corrected as shown below:

Claim 8, column 54, line 26, "$R^2$" should read --$R^1$--.

Signed and Sealed this

Eighth Day of September, 1998

Attest:

BRUCE LEHMAN

Attesting Officer

Commissioner of Patents and Trademarks